(12) United States Patent
Walker, II

(10) Patent No.: US 11,257,593 B2
(45) Date of Patent: *Feb. 22, 2022

(54) INTERACTIVE AND ANALYTICAL SYSTEM THAT PROVIDES A DYNAMIC TOOL FOR THERAPIES TO PREVENT AND CURE DEMENTIA-RELATED DISEASES

(71) Applicant: uMethod Health, Inc., Raleigh, NC (US)

(72) Inventor: John Quillian Walker, II, Raleigh, NC (US)

(73) Assignee: UMETHOD HEALTH, INC., Raleigh, NC (US)

( * ) Notice: Subject to any disclaimer, the term of this patent is extended or adjusted under 35 U.S.C. 154(b) by 132 days.

This patent is subject to a terminal disclaimer.

(21) Appl. No.: 16/665,862

(22) Filed: Oct. 28, 2019

(65) Prior Publication Data

US 2020/0058402 A1 Feb. 20, 2020

Related U.S. Application Data

(63) Continuation-in-part of application No. 14/788,770, filed on Jun. 30, 2015, now Pat. No. 10,460,842, (Continued)

(51) Int. Cl.
*G16H 50/20* (2018.01)
*G16H 50/30* (2018.01)

(52) U.S. Cl.
CPC ............ *G16H 50/20* (2018.01); *G16H 50/30* (2018.01)

(58) Field of Classification Search
CPC ......... A61K 47/60; G16H 50/20; G16H 50/30
See application file for complete search history.

(56) References Cited

U.S. PATENT DOCUMENTS 4,839,822 A 6/1989 Dormand et al.
4,974,254 A 11/1990 Perine et al.
(Continued)

FOREIGN PATENT DOCUMENTS

DE 102009018809 A1 10/2010
EP 1500025 B1 7/2008
(Continued)

OTHER PUBLICATIONS

Erin Allday, "Researchers dig deeper for Alzheimer's cure", 5 pages, Nov. 19, 2013, http://www.sfgate.com/health/article/Researchers-dig-deeper-for-Alzheimer-s-cure-499453 . . . .
(Continued)

*Primary Examiner* — Reginald R Reyes
(74) *Attorney, Agent, or Firm* — NK Patent Law

(57) ABSTRACT

A computer-implemented method, system, and apparatus for providing interactive and analytical components that provide a comprehensive and dynamic tool for therapies to prevent and cure dementia-related diseases. The invention includes one or more computers that receive and store personal information for people, including personal background information, pre-existing conditions, current medications, genomic data and diagnostic information. The computers also generate synergic data containing compounded probability data specifying an expected adjustment of individual biological mechanisms from particular combinations of therapies. For each person, the computers process personal information and identify a subset of biological mechanisms that are principally affected by dementia-related diseases or the substantial risk of dementia-related diseases. The computers also apply the personal information including the principally-affected biological mechanisms to the therapy data and generate for each person one or more messages communicating a therapy plan containing a com- (Continued)

bination of therapies and determines how to apply the therapies.

27 Claims, 11 Drawing Sheets

Related U.S. Application Data which is a continuation of application No. 14/167,943, filed on Jan. 29, 2014, now abandoned, application No. 16/665,862, which is a continuation of application No. 15/253,807, filed on Aug. 31, 2016, now abandoned, which is a continuation-in-part of application No. 15/243,908, filed on Aug. 22, 2016, now abandoned, said application No. 15/253,807 is a continuation-in-part of application No. 15/243,917, filed on Aug. 22, 2016, now abandoned, application No. 16/665,862, which is a continuation of application No. 15/253,818, filed on Aug. 31, 2016, now abandoned, which is a continuation-in-part of application No. 15/243,908, filed on Aug. 22, 2016, now abandoned, said application No. 15/253,818 is a continuation-in-part of application No. 15/243,917, filed on Aug. 22, 2016, now abandoned.

(60) Provisional application No. 62/208,606, filed on Aug. 22, 2015, provisional application No. 62/208,614, filed on Aug. 22, 2015, provisional application No. 62/212,528, filed on Aug. 31, 2015, provisional application No. 62/212,530, filed on Aug. 31, 2015.

(56) References Cited

U.S. PATENT DOCUMENTS

| | | | |
|---|---|---|---|
| 5,235,510 | A | 8/1993 | Yamada et al. |
| 5,245,995 | A | 9/1993 | Sullivan et al. |
| 5,255,187 | A | 10/1993 | Sorenson |
| 5,262,943 | A | 11/1993 | Thibado et al. |
| 5,769,074 | A | 6/1998 | Barnhill et al. |
| 5,983,379 | A | 11/1999 | Warren |
| 5,993,386 | A | 11/1999 | Ericsson |
| 6,024,699 | A | 2/2000 | Surwit et al. |
| 6,052,619 | A | 4/2000 | John |
| 6,081,786 | A | 6/2000 | Barry et al. |
| 6,126,596 | A | 10/2000 | Freedman |
| 6,165,126 | A | 12/2000 | Merzenich et al. |
| 6,188,988 | B1 | 2/2001 | Barry et al. |
| 6,223,074 | B1 | 4/2001 | Granger |
| 6,282,305 | B1 | 8/2001 | Huo et al. |
| 6,475,161 | B2 | 11/2002 | Teicher et al. |
| 6,523,009 | B1 | 2/2003 | Wilkins |
| 6,853,864 | B2 | 2/2005 | Litovitz |
| 6,876,972 | B1 | 4/2005 | Kameda |
| 7,029,275 | B2 | 4/2006 | Rubbert et al. |
| 7,299,192 | B2 | 11/2007 | Luttrell |
| 7,321,861 | B1 | 1/2008 | Oon |
| 7,366,572 | B2 | 4/2008 | Heruth et al. |
| 7,630,750 | B2 | 12/2009 | Liang et al. |
| 7,801,270 | B2 | 9/2010 | Nord et al. |
| 8,321,372 | B1 | 11/2012 | Rakshit et al. |
| 8,494,875 | B2 | 7/2013 | Broselow |
| 8,545,435 | B2 | 10/2013 | Bui |
| 10,276,260 | B2 | 4/2019 | Moturu et al. |
| 2002/0007286 | A1 | 1/2002 | Okamoto |
| 2002/0038227 | A1 | 3/2002 | Fey et al. |
| 2002/0107707 | A1 | 8/2002 | Naparstek et al. |
| 2002/0198742 | A1 | 12/2002 | Kameda et al. |
| 2003/0014284 | A1 | 1/2003 | Jones |
| 2003/0028399 | A1 | 2/2003 | Davis et al. |
| 2004/0006495 | A1 | 1/2004 | Dudley |
| 2005/0021240 | A1 | 1/2005 | Berlin et al. |
| 2005/0021679 | A1 | 1/2005 | Lightman et al. |
| 2006/0167529 | A1 | 7/2006 | Schecter |
| 2007/0122824 | A1 | 5/2007 | Tucker et al. |
| 2007/0172844 | A1 | 7/2007 | Lancaster et al. |
| 2008/0031406 | A1 | 2/2008 | Yan et al. |
| 2008/0118918 | A1* | 5/2008 | Licinio .................. G01N 33/74 435/6.16 |
| 2008/0182220 | A1 | 7/2008 | Chishti et al. |
| 2009/0012818 | A1 | 1/2009 | Rodgers |
| 2009/0220429 | A1 | 9/2009 | Johnsen et al. |
| 2009/0271008 | A1 | 10/2009 | Hyde et al. |
| 2010/0081971 | A1 | 4/2010 | Allison |
| 2011/0119212 | A1 | 5/2011 | De Bruin et al. |
| 2011/0159527 | A1 | 6/2011 | Schlossmacher et al. |
| 2011/0251854 | A1 | 10/2011 | Chung |
| 2012/0203573 | A1* | 8/2012 | Mayer .................... G16H 20/13 705/3 |
| 2012/0270190 | A1 | 10/2012 | Kenedy et al. |
| 2015/0025917 | A1 | 1/2015 | Stempora |
| 2015/0213232 | A1 | 7/2015 | Walker |
| 2015/0228062 | A1 | 8/2015 | Joshi et al. |
| 2016/0012749 | A1 | 1/2016 | Connor |
| 2017/0333733 | A1 | 11/2017 | Glimelius et al. |

FOREIGN PATENT DOCUMENTS

| | | |
|---|---|---|
| GB | 2354853 A | 4/2001 |
| WO | 2001039089 A1 | 5/2001 |
| WO | 2002067177 A2 | 8/2002 |
| WO | 03094092 A1 | 11/2003 |

OTHER PUBLICATIONS

David Perlmutter and Kristin Loberg,"Grain Brain, The Surprising Truth About Wheat, Carbs, and Sugar—Your Brain's Silent Killers", Little, Brown and Company, Sep. 2013, Chapters 7-9; 26 pages.

Doraiswamy, P., et al., "The Alzheimer's Action Plan", St. Martin's Griffin, May 2009, Chapters 6, 7, 8 and 10; pp. 72-138 and 164-177.

Tenenbaum, Jay M., et al., "Cancer: A Computational Disease That AI Can Cure", IAAI Articles, Ai Magazine, Summer 2011, pp. 14-26.

Gabhann, F., et al., "Multi-scale Computational Models of Pro-angiogenic Treatments in Peripheral Arterial Disease", Annals of Biomedical Engineering, vol. 35, No. 6, Jun. 2007, pp. 982-994.

Polaschek J., et al., "A Computer Program for Statistically-Based Decision Analysis", SCAMC, Inc., pp. 795-799.

Jansen, J., et al., "Teach-Discover-Treat (TDT): Collaborative computational drug discovery for neglected diseases", Elsevier, Journal of Molecular Graphics and Modelling, vol. 38, 2012, pp. 360-362.

Theendakara, V., et al., "Neuroprotective Sirtuin ratio reversed by ApoE4", PNAS Early Edition, pp. 1-6.

Small, G., et al., "The Alzheimer's Prevention Program: Keep Your Brain Healthy for the Rest of Your Life", The Alzheimer's Prevention Program, Dec. 11, 2012, https://www.amazon.com/Alzheimers-Prevention-Program-Brain-Healthy/dp/076117222X/.

Jean Carper, "100 Simple Things You Can Do to Prevent Alzheimer's and Age-Related Memory Loss", 6 pages, https://www.amazon.com/Simple-Things-Prevent-Alzheimers-Age-Related/dp/B005UVQBL6, Feb. 26, 2014.

USPTO; Final Office Action for U.S. Appl. No. 15/253,818 dated Jul. 31, 2019, 26 pages.

USPTO; Non-Final Office Action for U.S. Appl. No. 14/788,770 dated Mar. 5, 2019, 8 pages.

USPTO; Non-Final Office Action for U.S. Appl. No. 14/788,770 dated Sep. 10, 2015, 22 pages.

USPTO; Final Office Action for U.S. Appl. No. 14/788,770 dated Apr. 29, 2016, 9 pages.

USPTO; Non-Final Office Action for U.S. Appl. No. 15/243,908 dated Sep. 14, 2018, 27 pages.

USPTO; Final Office Action for U.S. Appl. No. 15/243,908 dated Apr. 2, 2019, 29 pages.

USPTO; Non-Final Office Action for U.S. Appl. No. 15/243,917 dated Oct. 5, 2018, 23 pages.

(56) References Cited

OTHER PUBLICATIONS

USPTO; Final Office Action for U.S. Appl. No. 15/243,917 dated Jun. 13, 2019 24 pages.
USPTO; Non-Final Office Action for U.S. Appl. No. 15/253,807 dated Oct. 30, 2018, 34 pages.
USPTO; Final Office Action for U.S. Appl. No. 15/253,807 dated Jul. 31, 2019, 33 pages.
USPTO; Non-Final Office Action for U.S. Appl. No. 15/253,818 dated Oct. 16, 2018, 28 pages.

* cited by examiner

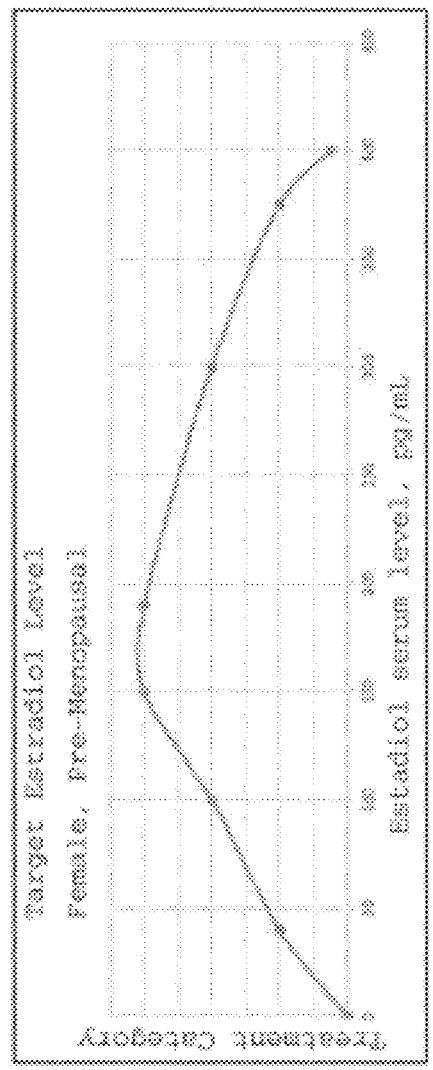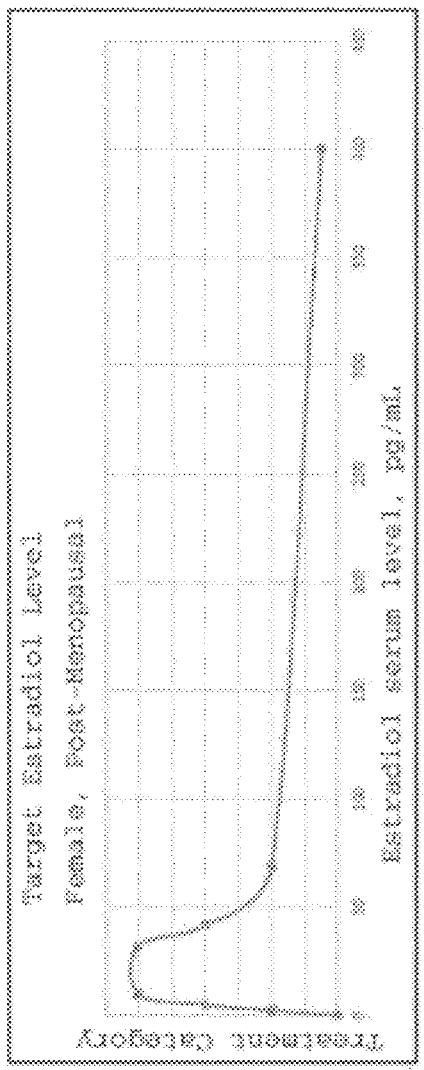
FIG. 10A
FIG. 10B

INTERACTIVE AND ANALYTICAL SYSTEM THAT PROVIDES A DYNAMIC TOOL FOR THERAPIES TO PREVENT AND CURE DEMENTIA-RELATED DISEASES

RELATED APPLICATIONS

This application is a continuation-in-part (CIP) of U.S. Utility application Ser. No. 14/788,770 entitled "INTERACTIVE AND ANALYTICAL SYSTEM THAT PROVIDES A DYNAMIC TOOL FOR THERAPIES TO PREVENT AND CURE DEMENTIA-RELATED DISEASES" filed Jun. 30, 2015, which is a continuation of U.S. Utility application Ser. No. 14/167,943 entitled "INTERACTIVE AND ANALYTICAL SYSTEM THAT PROVIDES A DYNAMIC TOOL FOR THERAPIES TO PREVENT AND CURE DEMENTIA-RELATED DISEASES" filed Jan. 29, 2014, all of which are commonly owned, the disclosures of which are all incorporated herein by reference in their entirety.

This application also claims priority to U.S. Utility application Ser. No. 15/243,908 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON MEASURED ANATOMICAL FEATURES" filed Aug. 22, 2016, which claims the benefit of U.S. Provisional Patent Application No. 62/208,606 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON MEASURED ANATOMICAL FEATURES", filed Aug. 22, 2015, and the benefit of U.S. Provisional Patent Application No. 62/208,614 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON IMAGED FOOD, DRINK, AND NUTRITIONAL INFORMATION", filed Aug. 22, 2015, and the benefit of U.S. Provisional Patent Application No. 62/212,528 entitled "INTERACTIVE AND ANALYTICAL MOBILE SYSTEM THAT PROVIDES A DYNAMIC TOOL FOR THERAPIES TO PREVENT AND CURE DEMENTIA-RELATED DISEASES", filed Aug. 31, 2015, and the benefit of U.S. Provisional Patent Application No. 62/212,530 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON A COMPLIANCE LEVEL OF A PATIENT WITH A THERAPY PLAN", filed Aug. 31, 2015, all of which are commonly owned, the disclosures of which are all incorporated herein by reference in their entirety.

This application also claims priority to U.S. Utility application Ser. No. 15/243,917 entitled "INTERACTIVE AND ANALYTICAL SYSTEM THAT PROVIDES A DYNAMIC TOOL FOR THERAPIES TO PREVENT AND CHANGE THE PROGRESSION OF DEMENTIA-RELATED DISEASES BASED ON IMAGED FOOD, DRINK, AND NUTRITIONAL INFORMATION", filed Aug. 22, 2016, which claims the benefit of U.S. Provisional Patent Application No. 62/208,606 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON MEASURED ANATOMICAL FEATURES", filed Aug. 22, 2015, and the benefit of U.S. Provisional Patent Application No. 62/208,614 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON IMAGED FOOD, DRINK, AND NUTRITIONAL INFORMATION", filed Aug. 22, 2015, and the benefit of U.S. Provisional Patent Application No. 62/212,528 entitled "INTERACTIVE AND ANALYTICAL MOBILE SYSTEM THAT PROVIDES A DYNAMIC TOOL FOR THERAPIES TO PREVENT AND CURE DEMENTIA-RELATED DISEASES", filed Aug. 31, 2015, and the benefit of U.S. Provisional Patent Application No. 62/212,530 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON A COMPLIANCE LEVEL OF A PATIENT WITH A THERAPY PLAN", filed Aug. 31, 2015, all of which are commonly owned, the disclosures of which are all incorporated herein by reference in their entirety.

This application also claims priority to U.S. Utility application Ser. No. 15/253,807 entitled "INTERACTIVE AND ANALYTICAL MOBILE SYSTEM THAT PROVIDES A DYNAMIC TOOL FOR THERAPIES TO PREVENT AND CHANGE THE PROGRESSION OF DEMENTIA-RELATED DISEASES", filed Aug. 31, 2016, which is a continuation-in-part of U.S. Utility application Ser. No. 15/243,908 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON MEASURED ANATOMICAL FEATURES" filed Aug. 22, 2016, which claims the benefit of U.S. Provisional Patent Application No. 62/208,606 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON MEASURED ANATOMICAL FEATURES", filed Aug. 22, 2015, all of which are commonly owned, the disclosures of which are all incorporated herein by reference in their entirety.

This application also claims priority to U.S. Utility application Ser. No. 15/253,807 entitled "INTERACTIVE AND ANALYTICAL MOBILE SYSTEM THAT PROVIDES A DYNAMIC TOOL FOR THERAPIES TO PREVENT AND CHANGE THE PROGRESSION OF DEMENTIA-RELATED DISEASES", filed Aug. 31, 2016, which is a continuation-in-part of U.S. Utility application Ser. No. 15/243,917 entitled "INTERACTIVE AND ANALYTICAL SYSTEM THAT PROVIDES A DYNAMIC TOOL FOR THERAPIES TO PREVENT AND CHANGE THE PROGRESSION OF DEMENTIA-RELATED DISEASES BASED ON IMAGED FOOD, DRINK, AND NUTRITIONAL INFORMATION" filed Aug. 22, 2016, which claims the benefit of U.S. Provisional Patent Application No. 62/208,614 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON IMAGED FOOD, DRINK, AND NUTRITIONAL INFORMATION", filed Aug. 22, 2015, and the benefit of U.S. Provisional Patent Application No. 62/212,528 entitled "INTERACTIVE AND ANALYTICAL MOBILE SYSTEM THAT PROVIDES A DYNAMIC TOOL FOR THERAPIES TO PREVENT AND CURE DEMENTIA-RELATED DISEASES", filed Aug. 31, 2015, and the benefit of U.S. Provisional Patent Application No. 62/212,530 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON A COMPLIANCE LEVEL OF A PATIENT WITH A THERAPY PLAN", filed Aug. 31, 2015, all of which are commonly owned, the disclosures of which are all incorporated herein by reference in their entirety.

This application also claims priority to U.S. Utility application Ser. No. 15/253,818 entitled "INTERACTIVE AND ANALYTICAL SYSTEM THAT PROVIDES A DYNAMIC TOOL FOR THERAPIES TO PREVENT AND CHANGE THE PROGRESSION OF DEMENTIA-RELATED DISEASES BASED ON A COMPLIANCE LEVEL OF A PATIENT WITH A THERAPY PLAN", filed Aug. 31, 2016, which is a continuation-in-part of U.S. Utility application Ser. No. 15/243,908 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON MEASURED ANATOMICAL FEATURES" filed Aug. 22, 2016, which claims the benefit of U.S. Provisional Patent Application No. 62/208,606 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON MEASURED ANATOMICAL FEATURES", filed Aug. 22, 2015, all of which are commonly owned, the disclosures of which are all incorporated herein by reference in their entirety.

This application also claims priority to U.S. Utility application Ser. No. 15/253,818 entitled "INTERACTIVE AND ANALYTICAL SYSTEM THAT PROVIDES A DYNAMIC TOOL FOR THERAPIES TO PREVENT AND CHANGE THE PROGRESSION OF DEMENTIA-RELATED DISEASES BASED ON A COMPLIANCE LEVEL OF A PATIENT WITH A THERAPY PLAN", filed Aug. 31, 2016, which is a continuation-in-part of U.S. Utility application Ser. No. 15/243,917 entitled "INTERACTIVE AND ANALYTICAL SYSTEM THAT PROVIDES A DYNAMIC TOOL FOR THERAPIES TO PREVENT AND CHANGE THE PROGRESSION OF DEMENTIA-RELATED DISEASES BASED ON IMAGED FOOD, DRINK, AND NUTRITIONAL INFORMATION" filed Aug. 22, 2016, which claims the benefit of U.S. Provisional Patent Application No. 62/208,614 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON IMAGED FOOD, DRINK, AND NUTRITIONAL INFORMATION", filed Aug. 22, 2015, all of which are commonly owned, the disclosures of which are all incorporated herein by reference in their entirety.

This application also claims priority to U.S. Utility application Ser. No. 15/253,818 entitled "INTERACTIVE AND ANALYTICAL SYSTEM THAT PROVIDES A DYNAMIC TOOL FOR THERAPIES TO PREVENT AND CHANGE THE PROGRESSION OF DEMENTIA-RELATED DISEASES BASED ON A COMPLIANCE LEVEL OF A PATIENT WITH A THERAPY PLAN", filed Aug. 31, 2016, which claims the benefit of U.S. Provisional Patent Application No. 62/212,528 entitled "INTERACTIVE AND ANALYTICAL MOBILE SYSTEM THAT PROVIDES A DYNAMIC TOOL FOR THERAPIES TO PREVENT AND CURE DEMENTIA-RELATED DISEASES", filed Aug. 31, 2015, and the benefit of U.S. Provisional Patent Application No. 62/212,530 entitled "INTERACTIVE AND ANALYTICAL SYSTEM THAT PROVIDES A DYNAMIC TOOL FOR THERAPIES TO PREVENT AND CURE DEMENTIA-RELATED DISEASES BASED ON A COMPLIANCE LEVEL OF A PATIENT WITH A THERAPY PLAN", filed Aug. 31, 2015, all of which are commonly owned, the disclosures of which are all incorporated herein by reference in their entirety.

FIELD OF THE INVENTION

The present invention relates to finding, preventing, slowing the progression of, and reversing the cognitive decline associated with dementia-related diseases, such as Alzheimer's disease or Lewy body dementia. The invention is, more specifically, a comprehensive and dynamic tool for therapies to prevent and reverse dementia-related diseases using interactive and analytic components.

BACKGROUND

The pressure to find treatments and preventions for Alzheimer's disease and other dementia-related diseases has been building steadily over the past decade, and it is becoming critical as the United States prepares for an increasing number of people who are approaching the age of 65, an age where the likelihood of the onset of dementia-related diseases increases. Aside from the personal losses to individuals and families, the needs of those patients will be an enormous burden on the nation's health care system, doctors say. In California alone, almost half a million people are living with Alzheimer's now, and that number is expected to climb to 660,000 by 2025, according to the Alzheimer's Association.

To date, no truly effective therapy has been developed for Alzheimer's disease or mild cognitive impairment.

SUMMARY OF THE INVENTION

In accordance with principles of embodiments of the present disclosure, systems, methods, apparatus, and computer-readable medium are provided to prevent, slow the progression of, and reverse the effects of dementia-related diseases.

One aspect disclosed and claimed herein comprises a computer-implemented method, system, apparatus and non-transitory media to interactive and analytical components that provides a comprehensive and dynamic tool for therapies to prevent, slow the progression of, or cure dementia-related diseases. The system comprises one or more computers, associated and connected non-transient electronic storage containing data and computer-executable instructions, and network communications connections with remote computers over networks. The one or more computers, electronic storage, and network communications connections together configure the computer system to receive and store personal information for people including personal and family background information, pre-existing conditions, current medications and diagnostic information containing data values for a diverse significantly-sized group of biological mechanisms that define dementia-related diseases as a medical condition or define a substantial risk of dementia-related diseases. The diverse significantly-sized group of biological mechanisms include a significant number of mechanisms that are used to help in the diagnosis or determination of the risk of a dementia-related disease. It should be appreciated that a significantly-sized group may include many different underlying biological mechanisms (and each having supporting data elements) that are recognized in clinical studies or publications to define or signify the existence or significant risk of existence of a dementia-related disease, such as Alzheimer's. For example, the number of underlying biological mechanisms may be 10, 15, 30, or 50 factors. The group is not limited to only these examples.

The one or more computers are also configured to receive and store therapy data that identifies individual therapies and specifies corresponding individual ones of the biological mechanisms that the therapy targets to adjust a physiological state of those corresponding biological mechanisms into recommended states for the disease for each biological mechanism, wherein the therapy data contains variations found in the individual therapy's effect on corresponding target biological mechanism as a function of a person's background data and also contains data quantifying a probability of success of the therapy. The one or more computers are configured to generate synergic data containing compounded probability data specifying an expected adjustment of individual biological mechanisms resulting from particular combinations of therapies and a probability reflecting the likelihood of reaching those therapy results.

The one or more computers are also configured for each person, to process personal information and as a result, identify a subset of the biological mechanisms that are principally affected by dementia-related diseases or a substantial risk of dementia-related diseases based on the biological mechanisms associated data value for that person. The one or more computers are configured to apply medical information, including the principally-affected biological mechanisms, data quantifying pre-existing conditions, and data specifying current medications, to the therapy data and generate, for each person, one or more messages communicating a therapy plan containing a combination of therapies and recommendations, and determines whether to apply the therapies in the therapy plan simultaneously, sequentially, or combinations thereof and the prescribed period for each therapy, wherein the therapy plan is selected from generating combinations of therapies that together have data characteristics that target biological mechanisms that are principally affected for that person, and the system generates the therapy plan by comparing probabilities of success of combinations of therapies and conflicts in components of therapies in therapy combinations and differentiating combinations using the probabilities and conflicts.

The one or more computers are configured to receive streams of diagnostic and testing data from diverse remote systems that generate current values associated with the biological mechanisms in people and applying the streams to monitor the status of the biological mechanisms in people during the therapy plan over time spans that are distanced shortly apart. The one or more computers are also configured to dynamically refine individual therapy plans when the monitoring determines at least one targeted biological mechanism, which was targeted for that person, is found to have been adjusted to be within a recommended target range for the disease, wherein modifying is performed by reapplying updated medical information and therapy information and generating a modified therapy plan. The one or more computers are configured to dynamically modify therapy data utilizing data from the data store to incorporate data from monitoring people and updating the probabilities and associated targeted biological mechanisms for individual therapies and combinations of therapies. The monitoring may include real-time monitoring of an individual with a device, such as a glucometer or a wearable heart monitor, an Internet-connected device that tracks the opening of medication caps, etc., or may also include processing the receipt of new information about a person. The concept of a "person's therapy team" is introduced here to describe the people who read, evaluate, and act upon the descriptions and recommendations that are the output of the computer system described in this invention. A person's therapy team might consist of one person only: a person interested in taking steps to improve their cognitive health or to prevent future dementia-related diseases. That person's personal physician might be further included in their team, as blood tests are administered to gain further insight. Note that this person might have no disease and no symptoms of disease. In contrast, for a person with advanced Alzheimer's disease, that person's therapy team might include themselves, multiple physicians and specialists, multiple caregivers, multiple family members, therapists, nurses, physician's assistants, and so on. The outputs of the computer system cater to the expectations and capabilities of the many potential members of the person's therapy team; the output may be in different spoken languages, at different grade levels, at different levels of medical expertise, and at different levels of confidentiality.

In one embodiment, the computer system is further configured to include a therapy optimization module that receives patient monitoring data and patient background information and modifies the therapy plan, wherein the modification optimizes a dosage in one of the therapies in the therapy plan. In another embodiment, the computer system is further configured to include a maintenance module that operates when the computer systems determines that a targeted biological mechanism for a person has been adjusted to be within the recommended target range for the disease and issues messages that contain a maintenance plan as part of the therapy plan that is determined to be issued and contains data that maintains the adjusted biological mechanism within the recommended target range for the disease. In yet another embodiment, the computer system is configured to accept as input additional relevant information about the individual, including the results of additional diagnostic testing before providing additional therapy. The updated patient information may include any type of new information that was not previously considered in the previous therapy plan. For example, the updated patient information may be diagnostic testing that has recently been performed or was inadvertently omitted from the patient information originally. Also, patient information may also include change in status information, such as the person is now going through menopause where the person was not previously going through menopause. These are just a few examples of what the updated patient information may include and are not limited to only these examples. In one embodiment, the computer system is configured to provide an interactive interface with which a person's therapy team interacts to view therapy plans, diagnostic information, or therapy progress.

In another embodiment, the computer system is configured to include network connections to the Internet for interacting with a person's therapy team and configured to include secured data storage that limits access to therapy and patient data based on credentials of requestor. In yet another embodiment, the list of actions includes questions that provide additional information that the system has identified to be most likely to lead to raising the likelihood of success with a current therapy or combination of therapies. In another embodiment, wherein the therapy plan additionally generates recommendations or a list of actions in a priority order. In another embodiment, the one or more computers are also configured to store data from a data store that includes a pool of data collected from people from various sources that document diagnostic and physical experiences of people having symptoms or therapy related to dementia-related diseases. In yet another embodiment, the one or more computers are also configured to configure a new therapy insertion module that receives new therapies and associated therapy data into the system and in response, the system automatically incorporates the new therapies in identifying therapy plans for people.

Another aspect of disclosed and claimed herein comprises a computer system that treats dementia-related diseases. The system comprise one or more computers, associated and connected non-transient electronic storage containing data and computer-executable instructions, and network communications connections with remote computers over networks. The computers, electronic storage, and network communications connections together configure the computer system to receive and store a stream of patient information containing patient background information, pre-existing conditions, current medications and diagnostic information containing data values for a diverse significantly-sized group of physiological mechanisms that define dementia-related diseases as a medical condition or define a substantial risk of dementia-related diseases as a medical condition. The one or more computers are also configured to receive and store a stream of therapy information containing individual therapies for the biological mechanisms and associated probabilities of success of the therapy in treating a corresponding biological mechanism based on base values of different patient background information.

The one or more computers are configured to process the patient information and therapy information and based on the processing identify specific combinations of therapies as individual therapy plans, wherein the specific combinations of therapies are individual best matches for a corresponding set of principally-affected biological mechanisms for people having certain corresponding sets of base values of background information, wherein the therapy plan additionally includes recommendations or a list of actions in a weighted or prioritized order. The one or more computers are also configured to store data from a data store that includes a pool of data collected from people from various sources that document diagnostic and physical experiences of people having symptoms or therapy related to dementia-related diseases. The one or more computers are configured to receive and process monitoring and tracking information containing values identifying current physiological states of the biological mechanisms for people and storing the values in association with the person and corresponding therapy and therapy plan. The one or more computers are also configured to determine from the stream of monitoring and tracking information whether one of a plurality of measurements associated with biological mechanisms for a person has been sufficiently adjusted and in response, modifying that patient therapy plan to target another biological mechanism and maintain operation of the adjusted mechanism. The one or more computers are configured to dynamically identify from the tracking and monitoring information including the measured physiological state of the biological mechanisms in the information a new therapy as a result of the system processing the stream of tracking and monitoring information from existing therapy plans, wherein the new therapy is defined by a new combination of therapies that will have combinational success based on processing the tracking and monitoring information. The one or more computers are also configured to dynamically modify or eliminate existing therapy plans when the stream of tracking and monitoring information from existing therapy plans shows that the actual performance is diverging into a negative direction. The one or more computers are configured to issue messages that communicate the new therapy or modified therapies to a doctor, health care provider, caregiver, or a person's computer devices.

The system can be implemented with specialized processing units such as with a personal information processing unit, a therapy data processing unit, a synergic data processing unit, a biological mechanism identifier unit, a data stream receiver unit and a therapy plan processing unit. Other processing units may be contemplated to provide described features or operations. These systems can include a processor, memory (RAM, ROM), communication interfaces (if applicable) and are configured to provide the above described corresponding operation or function.

A computer-readable storage medium such as a non-transitory computer readable medium can comprise instructions executed by a processor or electronic device to perform at least some of the steps of at least some of the system described herein (e.g., so as to provide features, functions, processes, or systems described herein).

It will be understood by those of ordinary skill in the art after reading the disclosure and as expressed herein that if desired, one or more features of elements of the exemplary system, method, or computer readable medium can be removed, modified, or re-arranged to arrive at a broader or different version of the system, method, or computer readable medium without departing from the spirit and scope of the invention.

Another aspect disclosed and claimed herein provides a monitoring server. The server is operable to receive participant information including structural and functional characteristics of an anatomical feature of a participant. The server is further operable to receive therapy plan information. The therapy plan information may include a plurality of individual therapy plans. Each individual therapy plan specifying an individual biological mechanism targeted for physiological adjustment, variations found in an effect on the targeted biological mechanism as a function of the participant information, and data quantifying a probability of success of the individual therapy plan. The server is operable to generate an aggregate therapy plan. The aggregate therapy plan targets adjustment of a plurality of biological mechanisms using a combination of the individual therapy plans. The aggregate therapy plan comprises an aggregate probability reflecting a likelihood of achieving all targeted adjustments. The server is operable to receive diagnostic and testing data associated with the participant. The diagnostic and testing data is captured after the participant has undergone treatment according to the aggregate therapy plan. For each individual therapy plan in the aggregate therapy plan, the server is operable to determine a value corresponding to the individual biological mechanism in the participant based on the received diagnostic and testing data and the participant information including the structural and functional characteristics of the anatomical feature of the participant. The server is further operable to perform a comparison of the value to a recommended range for the value, and, based on the comparison, dynamically adjust the individual therapy plan for the biological mechanism when the value is within the recommended range. The server is further operable to generate, for the participant, an adjusted aggregate therapy based on the individual therapy plan adjustments and adjust the therapy plan information based on success of the individual therapy plans of the participant and of other participants.

In one or more embodiments, participant data is provided at a participant device for use by a provider or the participant. The participant device is operable to receive provider data from a therapy provider.

In one or more embodiments, the server is operable to determine a freshness of the participant information.

In one or more embodiments, the server is operable to determine at least one item comprising the participant information is missing, and, in response to determining at least one item is missing, determine a criticality associated with the at least one item.

In one or more embodiments, the server is operable to receive the participant information from electronic health records.

In one or more embodiments, the server is operable to determine a participant's path to developing a dementia-related disease based on the participant information.

In one or more embodiments, the server is operable to determine a level of risk for the participant, and determine if the participant is a candidate based on the determined level of risk.

In one or more embodiments, the server is operable to prioritize ones of the biological mechanisms based on participant information and data associated with a group of participants.

In one or more embodiments, the server is operable to generate the aggregate therapy plan based on a priority of the biological mechanisms.

In one or more embodiments, the server is operable to store information regarding a participant's previous compliance with a previous aggregate therapy plan.

In one or more embodiments, the server is operable to adjust the therapy plan information based on the participant information and other participant information.

In one or more embodiments, the individual therapy plans include at least two therapy options where a second therapy option follows a first therapy option if the values of the biological mechanism are not within the recommended range.

In one or more embodiments, the anatomical feature is participant's brain.

In one or more embodiments, a structural characteristic of the structural and functional characteristics is at least one image.

In one or more embodiments, the server is operable to monitor the image for a change in one or more predefined areas of the participant's brain. The change relates to at least one of rate, direction, magnitude, or amount and progress of change.

In one or more embodiments, dynamically adjusting the therapy plan is based on a change of shrinkage rate or other functional characteristic for one of the one or more predefined areas.

In one or more embodiments, dynamically adjusting the therapy plan is based on a change in reverse shrinkage rate or other functional characteristic for one of the one or more predefined areas.

In one or more embodiments, the server is operable to receive data related to shrinkage rate and reverse shrinkage rate from a third party.

In one or more embodiments, the monitoring server is operable to compare the image of the brain with an expected result based on one or more characteristics of the participant, wherein the one or more characteristics include at least one of age, gender, culture, menopause status, prior injury or health defect.

In one or more embodiments, the participant device comprises one or more of a magnetic resonance imaging device, CT scanning device, PET scanning device, EEG scanner, MEG imaging device, and NIRS imaging device.

In one or more embodiments, structural characteristics includes at least one of volume, composition, density, placement, connections, surface and edge structure, and content of the anatomical feature.

In one or more embodiments, functional characteristics include one or more of a range of signal activity relating to the anatomical feature. The range of signal activity includes at least one of how much activity, its strength and dispersion, where it occurs spatially and structurally, its rate and periodicity, and its character.

Another aspect disclosed and claimed herein, a monitoring server is provided. The server includes a processor and a memory where the processor is operable to control the server to receive participant information including dietary and food intake information of a participant and receive therapy plan information. The therapy plan information may include a plurality of individual therapy plans, where each individual therapy plan specifies an individual biological mechanism targeted for physiological adjustment, variations found in an effect on the targeted biological mechanism as a function of the participant information, and data quantifying a probability of success of the individual therapy plan. The server is further operable to generate an aggregate therapy plan, wherein the aggregate therapy plan targets adjustment of a plurality of biological mechanisms using a combination of the individual therapy plans. The aggregate therapy plan includes an aggregate probability reflecting a likelihood of achieving all targeted adjustments. The server is further operable to receive diagnostic and testing data associated with the participant, wherein the diagnostic and testing data is captured after the participant has undergone treatment according to the aggregate therapy plan. For each individual therapy plan in the aggregate therapy plan, the server is further operable to determine a value corresponding to the individual biological mechanism in the participant based on the received diagnostic and testing data and the participant information including the dietary and food intake information of the participant, and perform a comparison of the value to a recommended range for the value. Based on the comparison, the server is further operable to dynamically adjust the individual therapy plan for the biological mechanism when the value is within the recommended range and generate, for the participant, an adjusted aggregate therapy based on the individual therapy plan adjustments, and adjust the therapy plan information based on success of the individual therapy plans of the participant and of other participants.

According to one or more embodiments, participant data is provided at a participant device for use by a provider or the participant, the participant device operable to receive provider data from a therapy provider.

According to one or more embodiments, wherein the participant device is a mobile device having an imaging device, whereby the participant images food to be consumed with the mobile device.

According to one or more embodiments, wherein the dietary and food intake information includes images of food to be consumed before consumption and after consumption.

According to one or more embodiments, wherein the server is operable to determine a characteristic of the imaged food based on color, color intensity, and color variation of the food.

According to one or more embodiments, wherein the server is operable to determine or receive information related to a mass, amount, or caloric intake of the imaged food.

According to one or more embodiments, wherein the monitoring server is operable to determine a freshness of the participant information.

According to one or more embodiments, wherein the monitoring server is operable to determine at least one item comprising the participant information is missing, and, in response to determining at least one item is missing, determine a criticality associated with the at least one item.

According to one or more embodiments, wherein the monitoring server is operable to receive the participant information from electronic health records.

According to one or more embodiments, wherein the monitoring server is operable to determine if the participant is a candidate for a dementia-related disease based on the participant information.

According to one or more embodiments, wherein the monitoring server is operable to determine a level of risk for the participant, and determine if the participant is a candidate based on the determined level of risk.

According to one or more embodiments, wherein the monitoring server is operable to prioritize ones of the biological mechanisms based on participant information and data associated with a group of participants.

According to one or more embodiments, wherein the monitoring server is operable to generate the aggregate therapy plan based on a priority of the biological mechanisms.

According to one or more embodiments, wherein the monitoring server is operable to store information regarding a participant's previous compliance with a previous aggregate therapy plan.

According to one or more embodiments, wherein the monitoring server is operable to adjust the therapy plan information based on the participant information and other participant information.

According to one or more embodiments, wherein the individual therapy plans include at least two therapy options where a second therapy option follows a first therapy option if the values of the biological mechanism are not within the recommended range.

According to one or more embodiments, wherein the server is operable to transmit instructions related to the treatment plan to a participant in response to determining a characteristic of the imaged food.

According to one or more embodiments, wherein the server is operable to store in a database one or more images of food and beverages being consumed by the participant and compare the one or more images of food and beverages being consumed by the participant to images of known foods and beverages.

According to one or more embodiments, wherein in order to generate the aggregate therapy plan further operable to determine frequency of meals, time of day of consumption, and other data based on the imaged food and beverage.

Another aspect disclosed and claimed herein, a participant device includes a first processor and a first memory operable to receive, in response to presenting at least a portion of an individual therapy plan, conformance information, send, to a monitoring server device, the conformance information, and a first display operable to present at least the portion of the individual therapy plan. A monitoring server device includes a second processor and a second memory operable to receive participant information including two or more of personal and family background data, pre-existing conditions, current medications, genomic data, and diagnostic information. The diagnostic information relates to biological mechanisms that define dementia-related diseases as a medical condition or risk of dementia-related diseases. The server is operable to receive therapy plan information. The therapy plan information includes a plurality of individual therapy plans, each individual therapy plan specifying an individual biological mechanism targeted for physiological adjustment, variations found in an effect on the targeted biological mechanism as a function of the participant information, and data quantifying a probability of success of the individual therapy plan. The server is operable to direct the participant device to display at least the portion of the individual therapy plan, receive, from the participant device, the conformance information, and generate an aggregate therapy plan, the aggregate therapy plan targeting adjustment of a plurality of biological mechanisms using a combination of the individual therapy plans, the aggregate therapy plan comprising an aggregate probability reflecting a likelihood of achieving all targeted adjustments. The server is operable to receive diagnostic and testing data associated with the participant, the diagnostic and testing data captured after the participant has undergone treatment according to the aggregate therapy plan. For each individual therapy plan in the aggregate therapy plan, the server is operable to determine a value corresponding to the individual biological mechanism in the participant based on the received diagnostic and testing data, perform a comparison of the value to a recommended range for the value, and based on the comparison, dynamically adjust the individual therapy plan for the biological mechanism when the value is within the recommended range, generate, for the participant, an adjusted aggregate therapy based on the individual therapy plan adjustments, and adjust the therapy plan information based on success of the individual therapy plans of the participant and of other participants.

According to one aspect, the participant device is further operable to receive provider data from a therapy provider.

According to one aspect, the monitoring server is further operable to determine a freshness of the participant information.

According to one aspect, the monitoring server is further operable to determine at least one item comprising the participant information is missing, and in response to determining at least one item is missing, determine a criticality associated with the at least one item.

According to one aspect, the monitoring server is further operable to receive the participant information from electronic health records.

According to one aspect, another monitoring server is operable to receive participant information from the monitoring server device.

According to one aspect, the another monitoring server is further operable to determine if the participant is a candidate for a dementia-related disease based on the participant information.

According to one aspect, the another monitoring server is further operable to determine a level of risk for the participant and determine if the participant is a viable candidate for a therapy based on a determined level of risk.

According to one aspect, the monitoring server is further operable to prioritize the plurality of biological mechanisms based on participant information and data associated with a group of participants.

According to one aspect, the monitoring server is further operable to generate the aggregate therapy plan based on a priority of the biological mechanisms.

According to one aspect, the monitoring server is further operable to store information regarding a participant's previous compliance with a previous aggregate therapy plan.

According to one aspect, the monitoring server is further operable to adjust the therapy plan information based on the participant information and other participant information.

According to one aspect, the individual therapy plans include at least two therapy options where a second therapy option follows a first therapy option if the values of the biological mechanism are not within the recommended range.

According to one aspect, the participant device is configured with a participant application software client.

According to one aspect, the monitoring server is further operable to track adherence to the therapy plan, and to show the therapy plan to the participant as appropriate.

According to one aspect, the monitoring server is further operable to determine a participant's prognosis based on one or more of cognitive status and risk/health indices, and send, to the participant device, the participant's prognosis.

According to one aspect, the participant device is further operable to receive, at the participant device, direct data input from the participant and their therapy team, and receive, at the participant device, personal logging of observations and adherence information.

According to one aspect, the monitoring server is further operable to direct the participant device to provide one or more of training videos and a frequently asked questions database that is accessible by the participant device.

According to one aspect, the monitoring server is further operable to authenticate a user by one or more of a finger print, facial recognition, and other biometric characteristic.

According to one aspect, the participant application software client is dynamic and personalized to current needs, coaching methodology and stage of coaching of a person.

According to one aspect, the participant application software client is integrated with native environment resources comprising one or more of a calendar, ehealth functions, and notifications.

According to one aspect, the participant device is further operable to prompt the participant for interaction one of a minimum of twice a day, and in morning and evening, and adjust a prompting frequency based on a level of compliance.

According to one aspect, the participant device is further operable to collect first cognitive information, the first cognitive information comprising participant answers to a corresponding one or more questions, collect second cognitive information, the second cognitive information comprising one or more videos reflecting participant behavior to one or more prompts, and send, to the monitoring server, the first cognitive information and second cognitive information. The monitoring server is further operable to receive, from the participant device, the first cognitive information and second cognitive information, and assess, based on the first cognitive information and second cognitive information, a cognitive state of the participant.

According to one aspect, the first cognitive information is further determined based on one or more of participant performance in a series of games, participant performance in standardized cognitive tests, and participant performance in behavioral exercises.

According to one aspect, the participant device is further operable to scan medication packets for one or more of a bar code, QR code, and a SKU, and send, to the monitoring server device, information reflecting the scanned medication packets. The monitoring server is further operable to receive, from the participant device, information reflecting the scanned medication packets, link to a database of medications for use in application of the therapy plan, designate a medication based on the database of medications and the scanned medication packets, and send medication information identifying the medication to the participant device.

According to one aspect, the participant device is further operable to collect the conformance information based on monitoring of one or more of how often medication packets are scanned, when medication packets are scanned, what foods have been eaten before taking medication, and what foods have been eaten after taking medication. The participant device is further operable to send, to the monitoring server device, the conformance information. The monitoring server is further operable to determine compliance information based on the conformance information.

According to one aspect, the monitoring server is further operable to perform a comparison of compliance information to a threshold, and based on the comparison, send to the participant device, an alert. The participant device is further operable to receive, from the monitoring server device, the alert, and in response to receiving the alert, prompt the participant.

Another aspect disclosed and claimed herein, a participant device that includes a first processor and a first memory operable to collect, based on monitoring instruction information, conformance information for the participant and send, to a monitoring server device, the conformance information. The device is further operable to receive, from the monitoring server device, updated monitoring instruction information, and adjust, based on the monitoring instruction information, the collection of conformance information for the participant. The monitoring server includes a second processor and a second memory operable to receive participant information including two or more of personal and family background data, pre-existing conditions, current medications, genomic data, and diagnostic information, the diagnostic information relating to biological mechanisms that define dementia-related diseases as a medical condition or risk of dementia-related diseases and receive therapy plan information, the therapy plan information comprising a plurality of individual therapy plans, each individual therapy plan specifying an individual biological mechanism targeted for physiological adjustment, variations found in an effect on the targeted biological mechanism as a function of the participant information, and data quantifying a probability of success of the individual therapy plan. The server is further operable to generate an aggregate therapy plan, the aggregate therapy plan targeting adjustment of a plurality of biological mechanisms using a combination of the individual therapy plans, the aggregate therapy plan comprising an aggregate probability reflecting a likelihood of achieving all targeted adjustments. The server is further operable to receive diagnostic and testing data associated with the participant, the diagnostic and testing data captured after the participant has undergone treatment according to the aggregate therapy plan. Tor each individual therapy plan in the aggregate therapy plan, the server is further operable to determine a value corresponding to the individual biological mechanism in the participant based on the received diagnostic and testing data, perform a comparison of the value to a recommended range for the value, and based on the comparison, dynamically adjust the individual therapy plan for the biological mechanism when the value is within the recommended range. The server is further operable to generate, for the participant, an adjusted aggregate therapy based on the individual therapy plan adjustments, adjust the therapy plan information based on success of the individual therapy plans of the participant and of other participants, and receive, from the participant device, conformance information. The server is further operable to determine, from the conformance information, a level of conformance, update, based on the level of conformance, monitoring instruction information, and send, to the participant device, the updated monitoring instruction information.

According to one aspect, the participant device is further operable to increase a rate of collection of conformance information for the participant.

According to one aspect, the participant device is further operable to adjust, based on the monitoring instruction information, the collection of conformance information for the participant, and decrease a rate of collection of conformance information for the participant.

According to one aspect, the participant device is a digital assistant.

According to one aspect, the participant device is a mobile device.

According to one aspect, the mobile device is a wearable device such as a fitness tracker.

According to one aspect, the participant device is two participant devices. A first participant device is a proxy device, and a second participant device is a medical monitoring device, wherein the first participant device and the second participant device are connected through a network.

According to one aspect, the network is a Bluetooth network.

According to one aspect, the proxy device is one of a smart phone, smart watch, and a tablet.

According to one aspect, the medical monitoring device is one or more of a CPAP and a glucometer.

According to one aspect, the participant device is further operable to receive provider data from a therapy provider.

According to one aspect, the monitoring server is further operable to determine a freshness of the participant information.

According to one aspect, the monitoring server is further operable to determine at least one item comprising the participant information is missing, and in response to determining at least one item is missing, determine a criticality associated with the at least one item.

According to one aspect, the monitoring server is further operable to receive the participant information from electronic health records.

According to one aspect, another monitoring server is operable to receive participant information from the monitoring server device.

According to one aspect, the another monitoring server is further operable to determine if the participant is a candidate for a dementia-related disease based on the participant information.

According to one aspect, the another monitoring server is further operable to determine a level of risk for the participant and determine if the participant is a viable candidate for a therapy based on a determined level of risk.

According to one aspect, the monitoring server is further operable to prioritize the plurality of biological mechanisms based on participant information and data associated with a group of participants.

According to one aspect, the monitoring server is further operable to generate the aggregate therapy plan based on a priority of the biological mechanisms.

According to one aspect, the monitoring server is further operable to store information regarding a participant's previous compliance with a previous aggregate therapy plan.

According to one aspect, the monitoring server is further operable to adjust the therapy plan information based on the participant information and other participant information.

According to one aspect, the individual therapy plans include at least two therapy options where a second therapy option follows a first therapy option if the values of the biological mechanism are not within the recommended range.

According to one aspect, the participant device is configured with a participant application software client.

According to one aspect, the monitoring server is further operable to track adherence to the therapy plan, and to show the therapy plan to the participant as appropriate.

According to one aspect, the monitoring server is further operable to determine a participant's prognosis based on one or more of cognitive status and risk/health indices, and send, to the participant device, the participant's prognosis.

According to one aspect, the participant device is further operable to receive, at the participant device, direct data input from the participant and their therapy team, and receive, at the participant device, personal logging of observations and adherence information.

According to one aspect, the monitoring server is further operable to direct the participant device to provide one or more of training videos and a frequently asked questions database that is accessible by the participant device.

According to one aspect, the monitoring server is further operable to authenticate a user by one or more of a finger print, facial recognition, and other biometric characteristic.

According to one aspect, the participant application software client is dynamic and personalized to current needs, coaching methodology and stage of coaching of a person.

According to one aspect, the participant application software client is integrated with native environment resources comprising one or more of a calendar, ehealth functions, and notifications.

According to one aspect, the participant device is further operable to prompt the participant for interaction one of a minimum of twice a day, and in morning and evening, and adjust a prompting frequency based on a level of compliance.

According to one aspect, the participant device is further operable to collect first cognitive information, the first cognitive information comprising participant answers to a corresponding one or more questions, collect second cognitive information, the second cognitive information comprising one or more videos reflecting participant behavior to one or more prompts, and send, to the monitoring server, the first cognitive information and second cognitive information. The monitoring server is further operable to receive, from the participant device, the first cognitive information and second cognitive information, and assess, based on the first cognitive information and second cognitive information, a cognitive state of the participant.

According to one aspect, the monitoring server is further operable to perform a comparison of compliance information to a threshold, and based on the comparison, send to the participant device, an alert. The participant device is further operable to receive, from the monitoring server device, the alert, and in response to receiving the alert, prompt the participant.

It will be understood by those of ordinary skill in the art after reading the disclosure and as expressed herein that if desired, one or more features of elements of the exemplary system, method, or computer readable medium can be removed, modified, or re-arranged to arrive at a broader or different version of the system, method, or computer readable medium without departing from the spirit and scope of the invention.

BRIEF DESCRIPTION OF THE DRAWINGS

Figure 1:
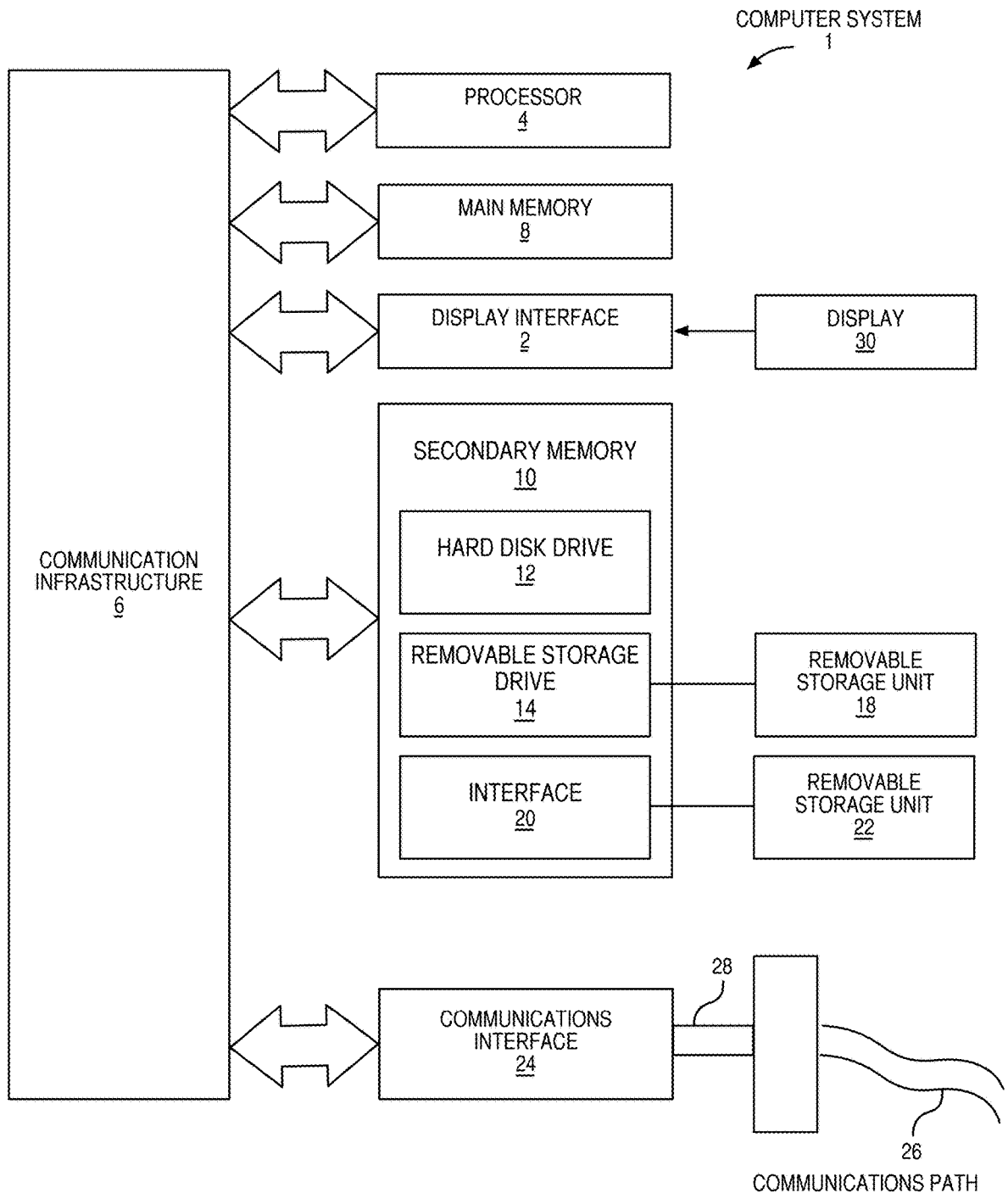
Figure 2:
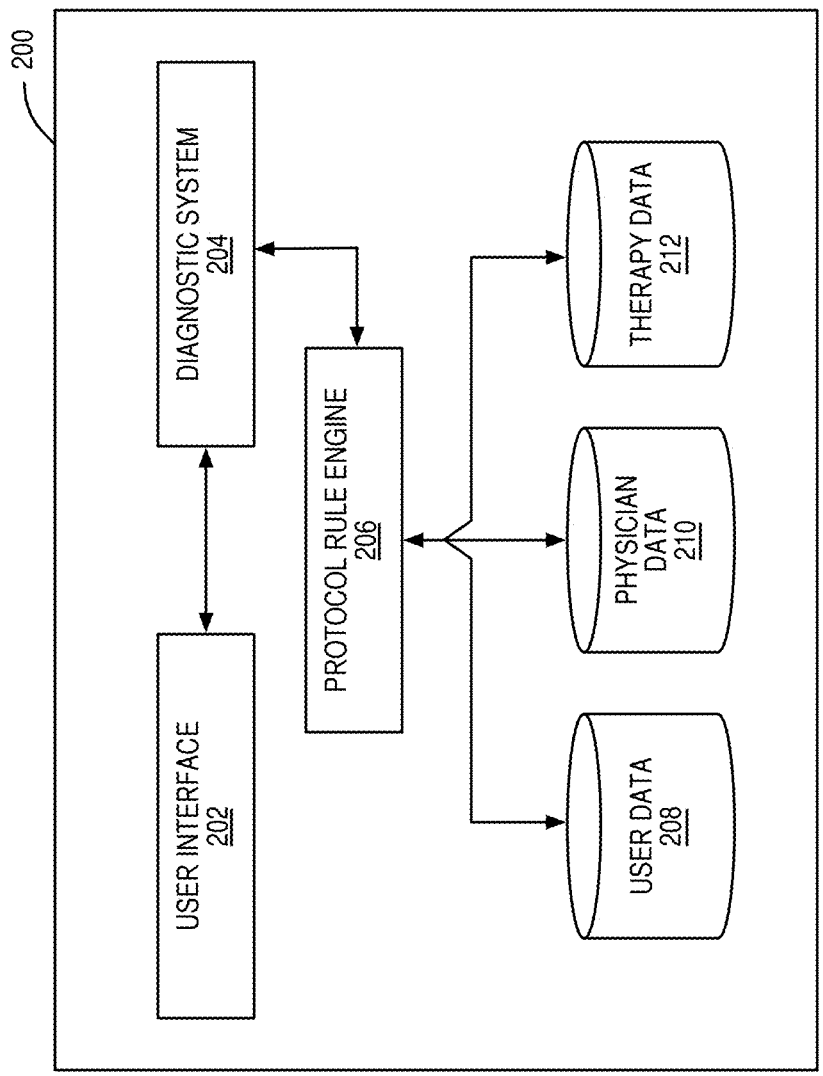
Figure 3:
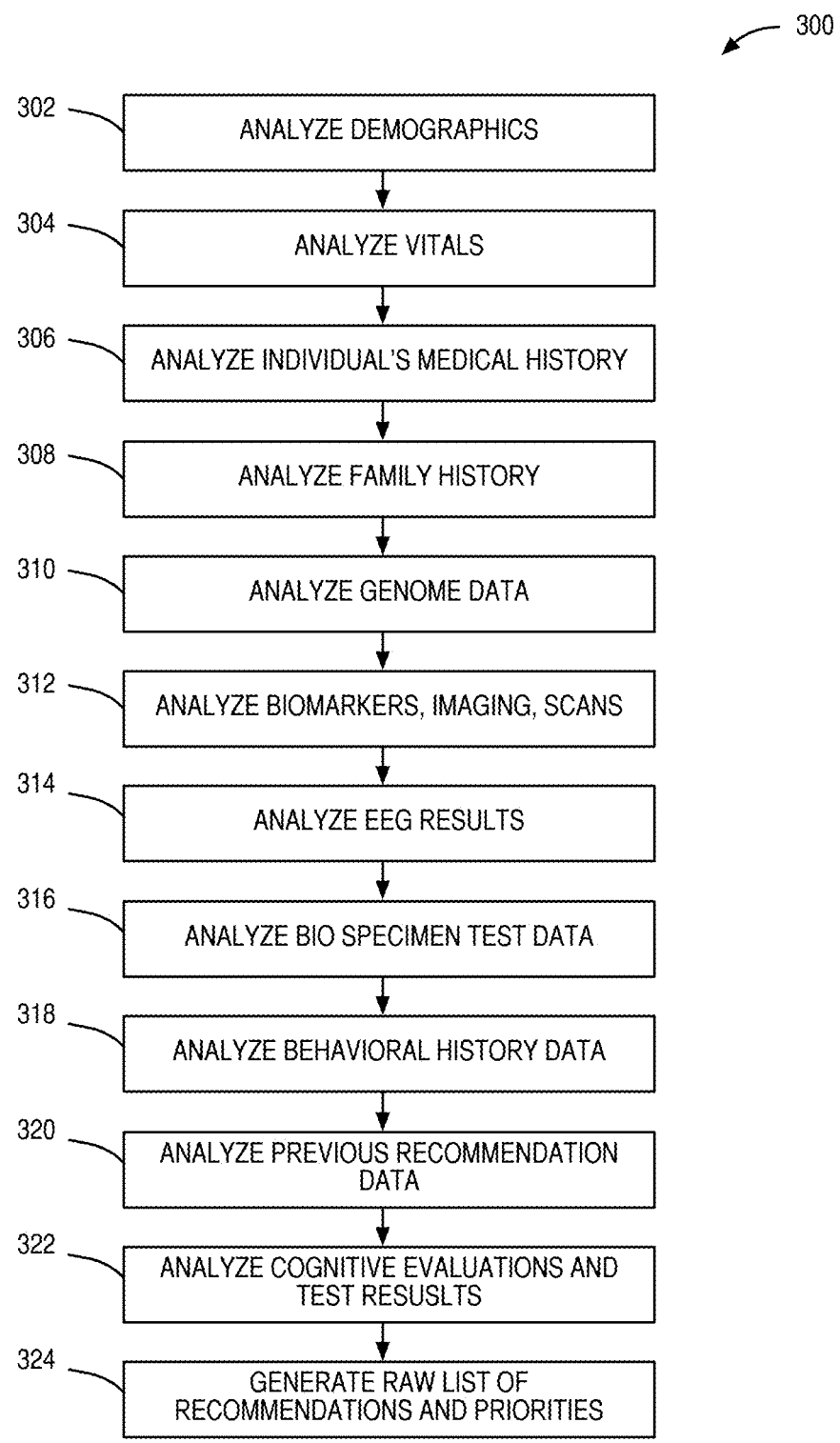
Figure 4:
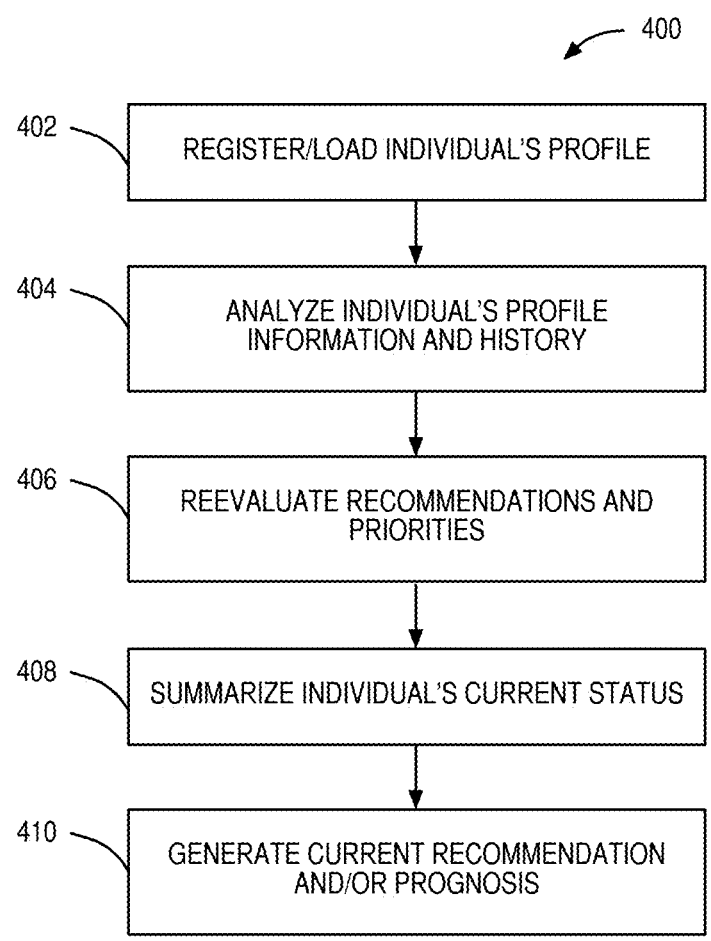
Figure 5:
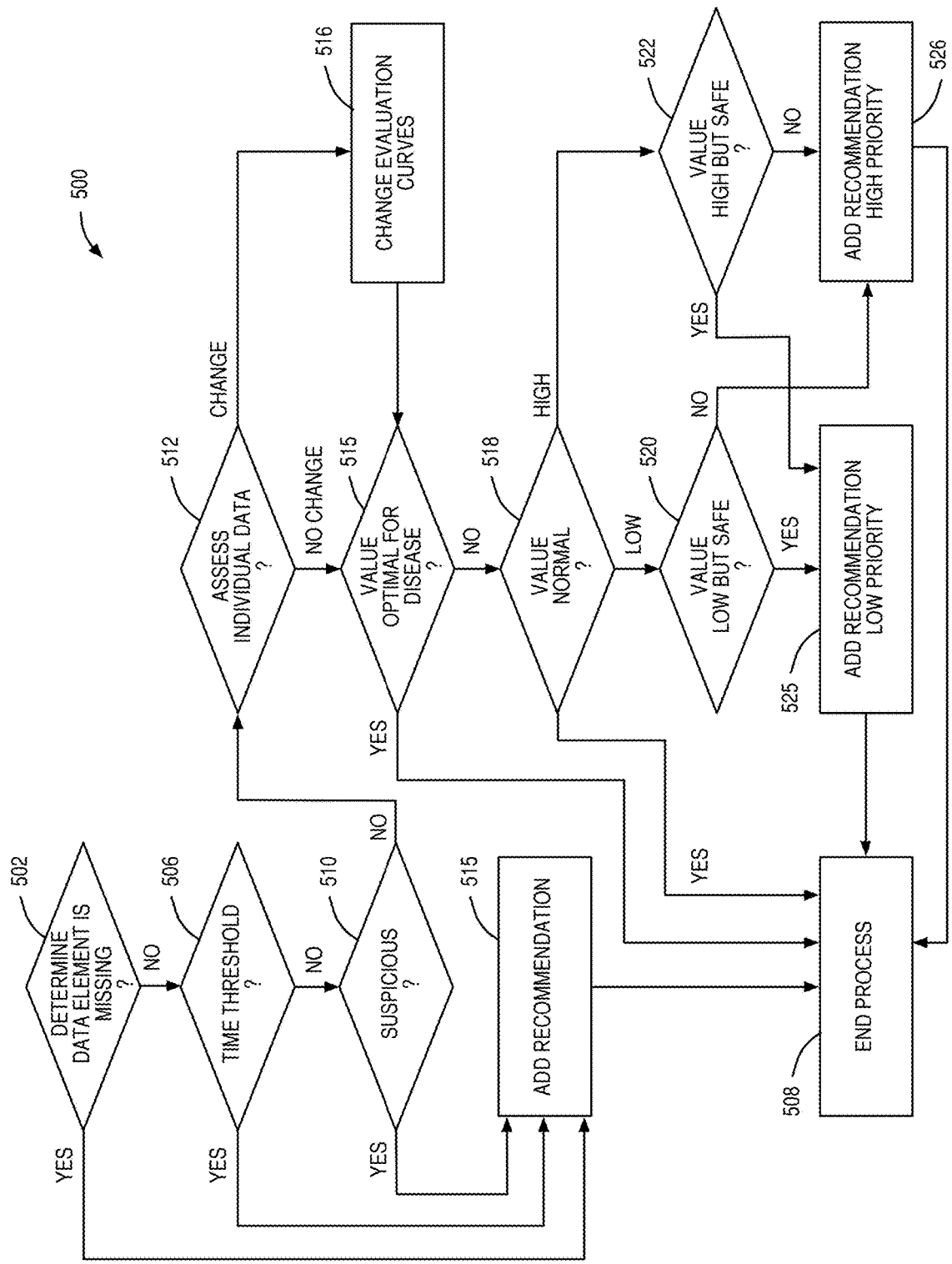
Figure 6:
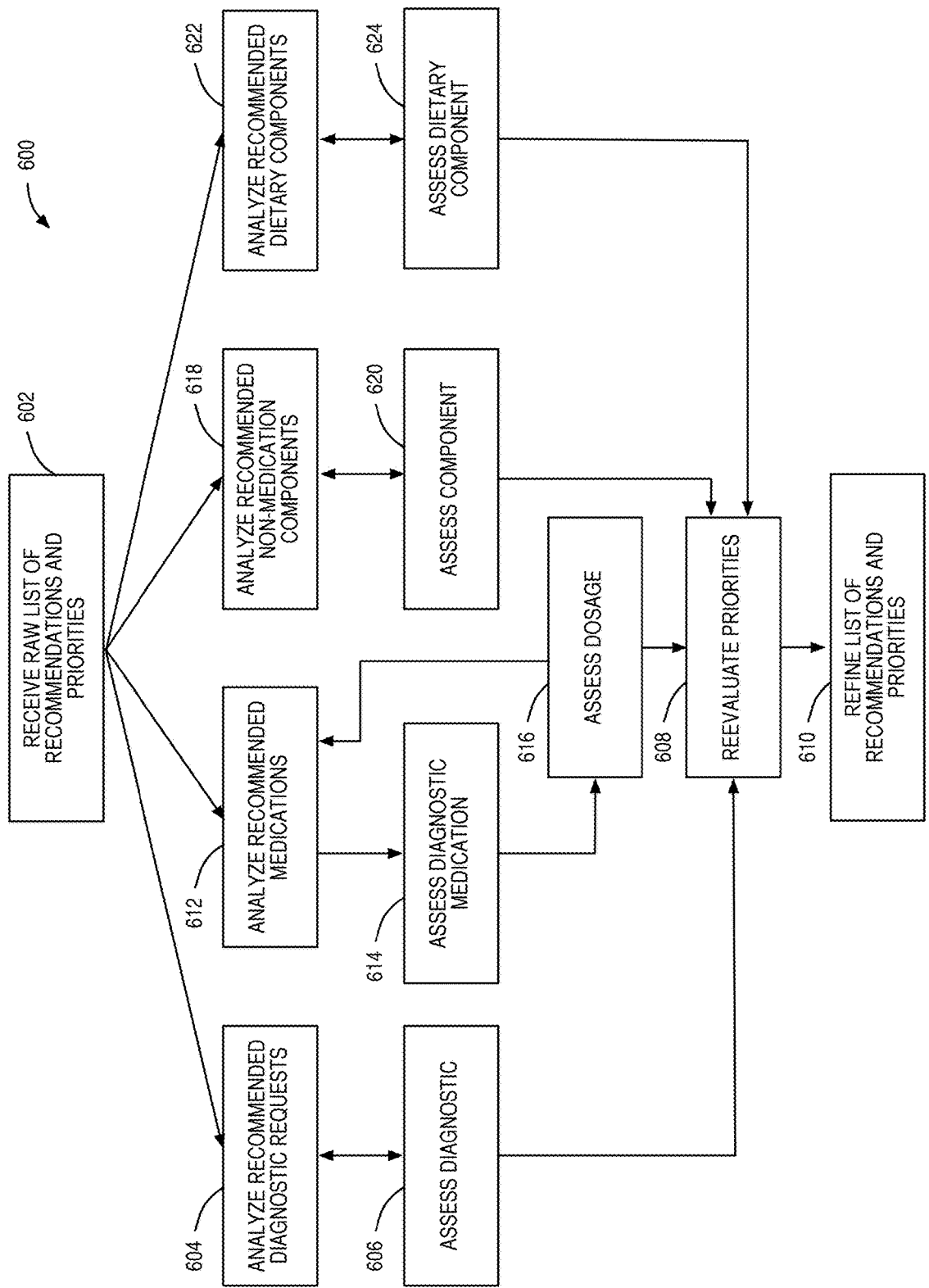
Figure 7:
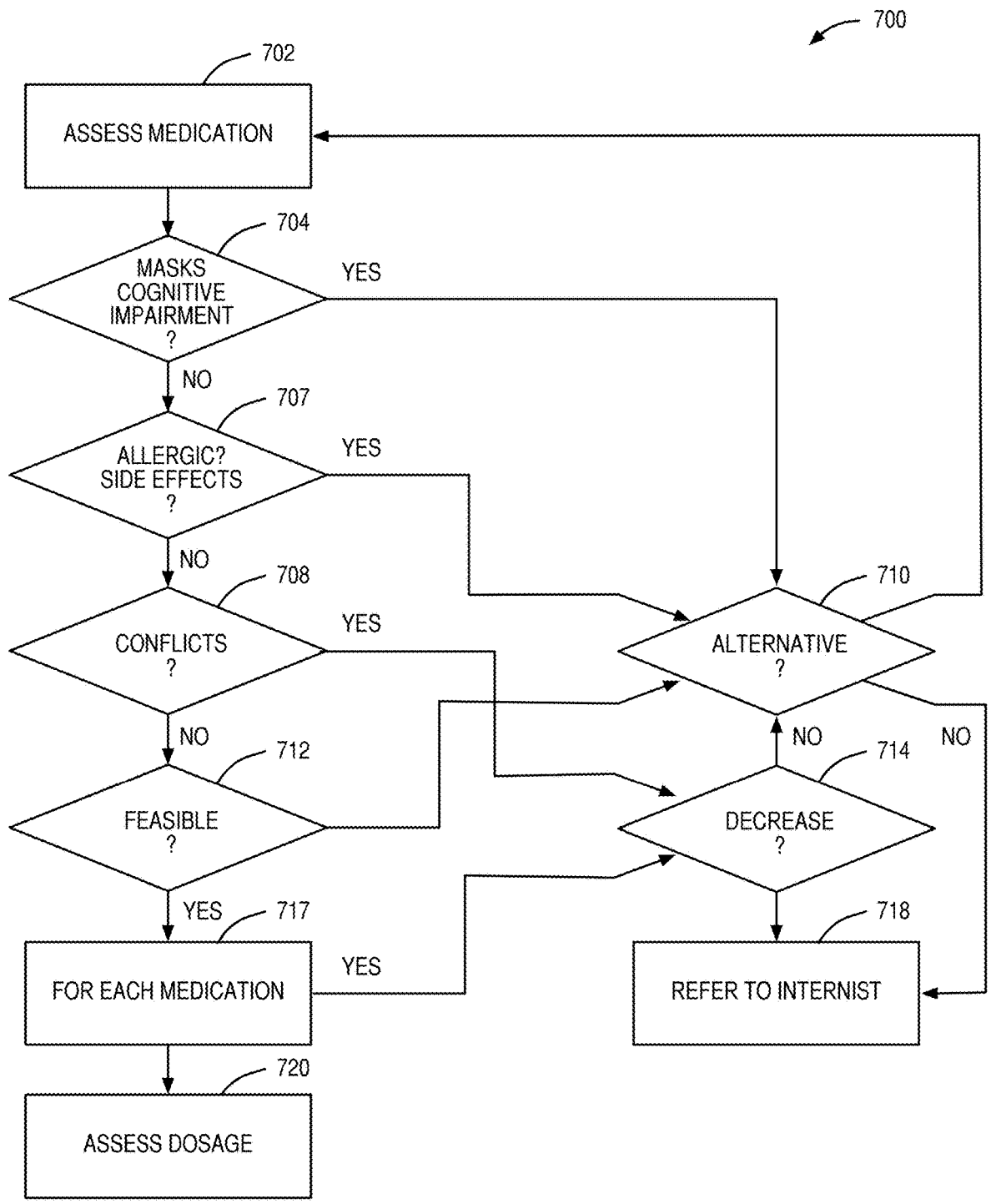
Figure 8:
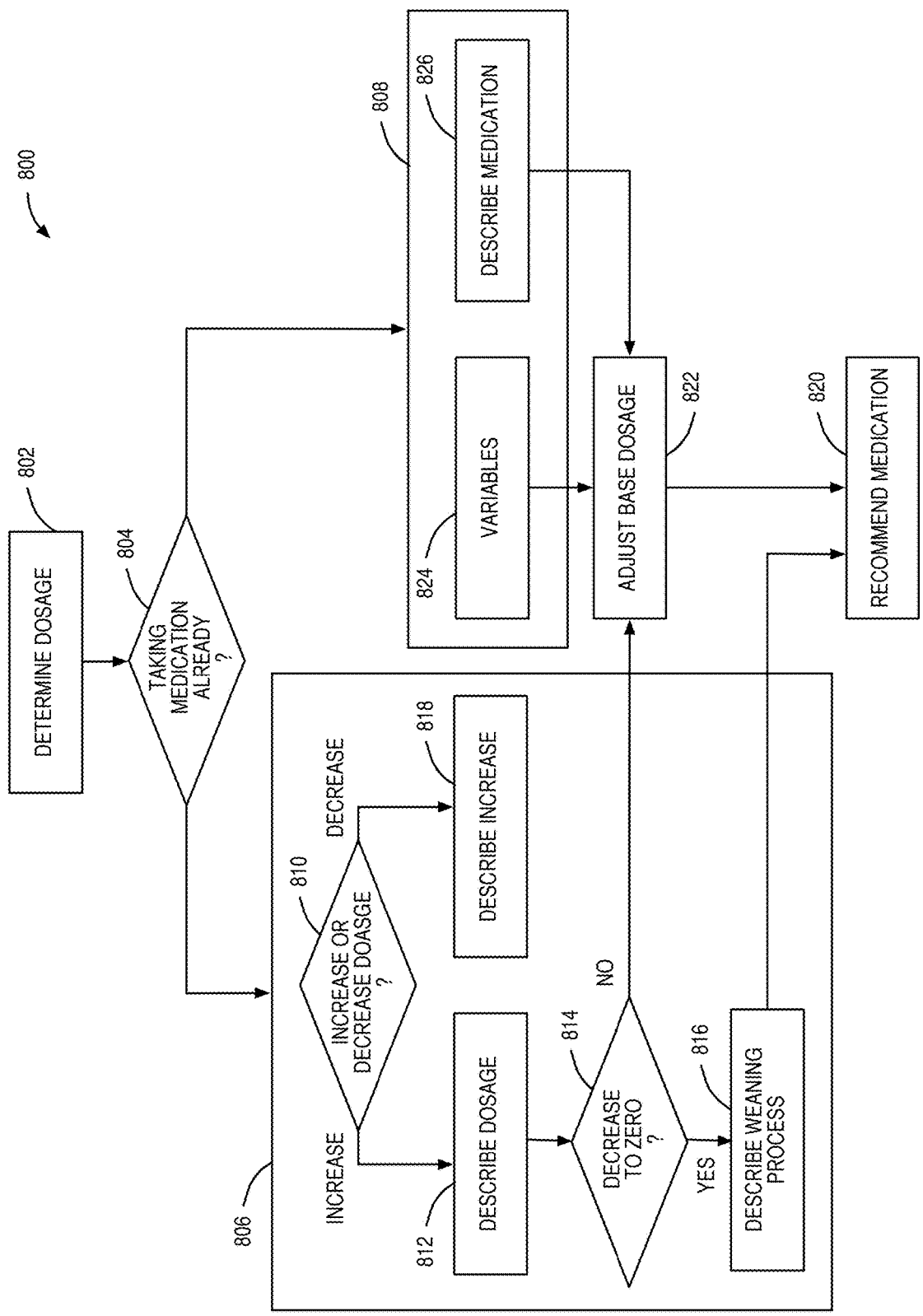
Figure 9:
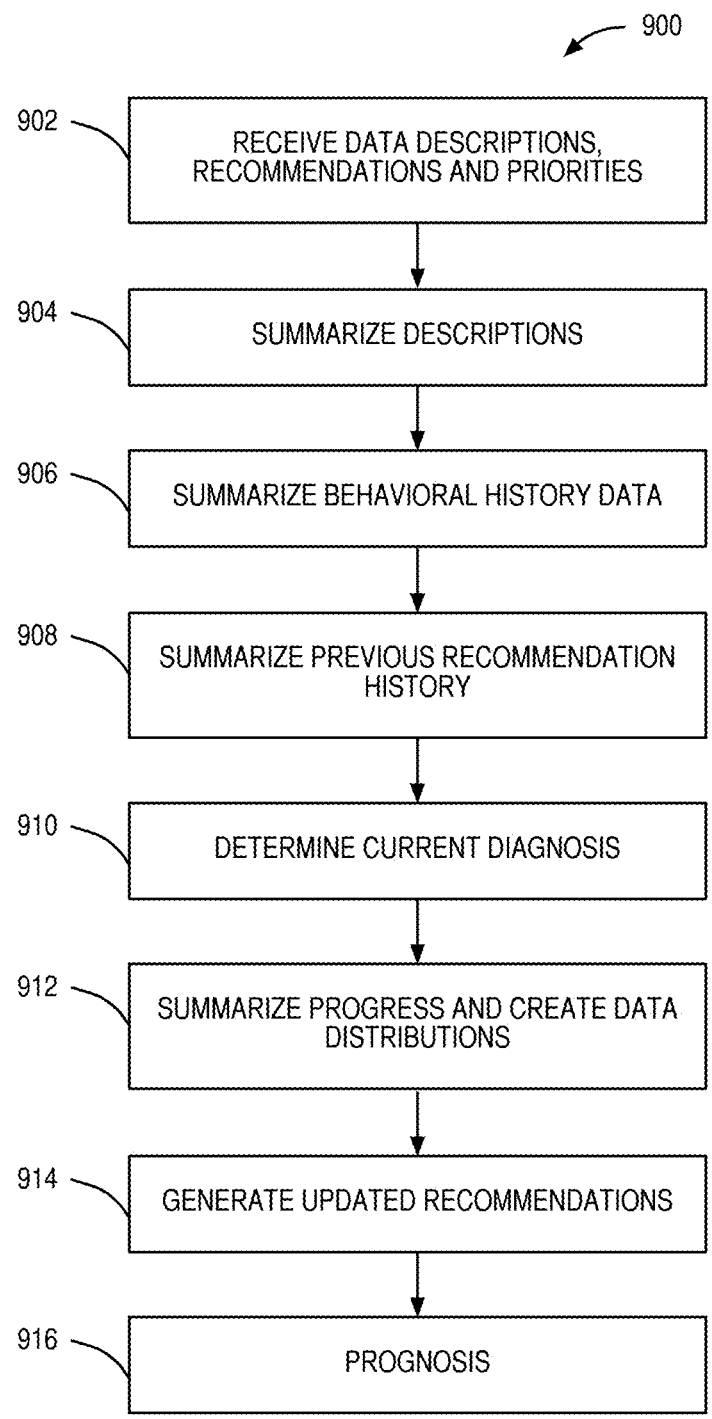
Figure 11:
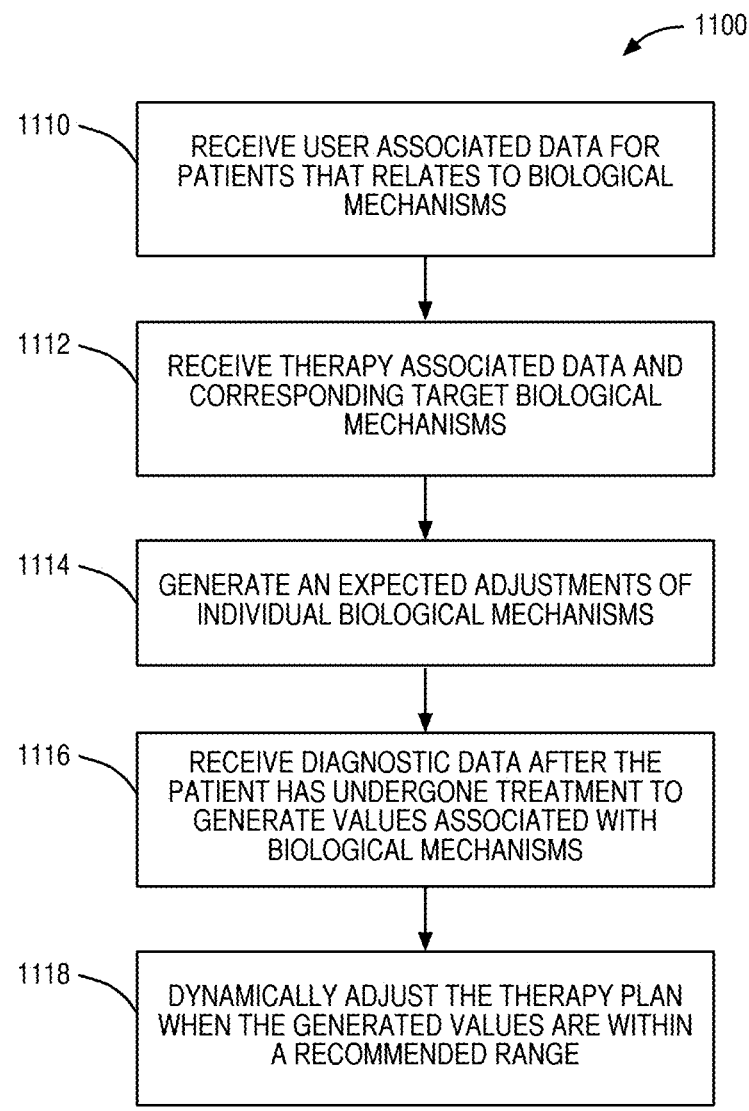

Having thus described preferred and exemplary embodiments of the present invention in general terms, reference will now be made to the accompanying drawings, which are not necessarily drawn to scale, and wherein:

FIG. 1 illustrates a block diagram with various computer system components for use with an exemplary implementation of a system for a comprehensive and dynamic tool for therapies to prevent and change the progression of dementia-related diseases, in accordance with one embodiment of the present invention;

FIG. 2 illustrates a system diagram of components for a comprehensive and dynamic tool for therapies to prevent and change the progression of dementia-related diseases, in accordance with one embodiment of the present invention;

FIG. 3 is a schematic flow diagram of the process of evaluating a person's data to create a raw list of recommendations and priorities, in accordance with one embodiment of the present invention;

FIG. 4 is a schematic flow diagram of the process of evaluating each data element in the system, in accordance with one embodiment of the present invention;

FIG. 5 is a schematic flow diagram of the process of reevaluating the list of recommendations for a person's therapy team, in accordance with one embodiment of the present invention;

FIG. 6 is a schematic flow diagram of the process of assessing and updating a medication or treatment recommendation, in accordance with one embodiment of the present invention;

FIG. 7 is a schematic flow diagram of the process of assessing and updating a medication dosage recommendation, in accordance with one embodiment of the present invention;

FIG. 8 is a schematic flow diagram of the process describing a person's current status for the person's therapy team, in accordance with one embodiment of the present invention;

FIG. 9 is a schematic flow diagram of a person's process of the comprehensive and dynamic tool for therapies to prevent and change the progression of dementia-related diseases, in accordance with one embodiment of the present invention;

FIGS. 10A and 10B illustrate evaluation curves for a participant produced according to the systems and methods disclosed herein; and FIG. 11 is a schematic flow diagram of one or more methods disclosed herein.

DETAILED DESCRIPTION

In approaching the treatment of therapies to prevent and change the progression of dementia-related diseases one approach has been to focus on one aspect of the change in brain physiology, the level of amyloid beta. This focus has been a twofold problem. First, amyloid beta is most likely one piece of a long chain of events that go wrong in the brains of people with Alzheimer's disease. And second, the plaque buildup likely has been going on for years, even decades, before people are symptomatic. In the past 10 years, amyloid therapies have failed, one after another, to provide significant benefit to people even with mild dementia. That is not to say that scientists are giving up on amyloid beta, and it's still a primary focus of Alzheimer's research. The scientific community and the major drug developers have devoted decades of resources into studying amyloid beta. There is little doubt that the protein is important, and it may indeed be a viable target for drugs to treat the disease someday. But in the meantime, scientists are looking for other targets, and they are trying to dig much deeper into the history of the disease and identify the earliest signs of it in people who are not yet symptomatic.

At Stanford, scientists have focused on the communication lines, called synapses, which allow neurons in the brain to interact with one another. Synapses are created to help build memories and learn new skills, but synapses also must be pruned to keep brain activity healthy and efficient. Scientists are coming to believe that in brains afflicted by Alzheimer's disease, that pruning process becomes overactive. Synapses that help people retain memories and create new ones are snipped and cannot be repaired. Eventually, the neurons on either end of the synaptic connections die. A current idea is that the disease starts earlier than previously thought.

To study the earliest phases of a disease, scientists seek to be able to identify individual persons long before they complain of symptoms like memory loss. That is why the most attractive targets for early Alzheimer's disease interventions may be found in people who are known to have a genetic risk for the disease. There has been growing interest in the gene called ApoE (Apolipoprotein E), in particular. There are three versions (isoforms) of the gene, and one of them, known as ApoE epsilon 4 (e4), is associated with an increased risk of developing Alzheimer's disease. People with one copy of ApoE e4 are three times more likely to get Alzheimer's than someone with a healthy variant; two copies of e4 increase the risk 10- to 12-fold.

The focus of most development efforts has been directed to monotherapies. These efforts have been deficient in providing a significant improvement in treating Alzheimer's.

To date, no truly effective therapy has been developed for Alzheimer's disease or mild cognitive impairment.

Aspects of the present disclosure now will be described more fully hereinafter with reference to the accompanying drawings The present disclosure is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Throughout this specification, like reference numbers signify the same elements throughout the description of the figures.

When elements are referred to as being "connected" or "coupled", the elements can be directly connected or coupled together or one or more intervening elements may also be present. In contrast, when elements are referred to as being "directly connected" or "directly coupled," there are no intervening elements present.

The subject matter may be embodied as devices, systems, methods, and/or computer program products. Accordingly, some or all of the subject matter may be embodied in hardware and/or in software (including firmware, resident software, micro-code, state machines, gate arrays, etc.) Furthermore, the subject matter may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be for example, but not limited to, an electronic, magnetic, optical, electromagnetic, infrared, or semiconductor system, apparatus, device, or propagation medium. By way of example, and not limitation, computer-readable media may comprise computer storage media and communication media.

Computer storage media is non-transitory and includes volatile and nonvolatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage components, or any other medium which can be used to store the desired information and may be accessed by an instruction execution system. Note that the computer-usable or computer-readable medium can be paper or other suitable medium upon which the program is printed, as the program can be electronically captured via, for instance, optical scanning of the paper or other suitable medium, then compiled, interpreted, of otherwise processed in a suitable manner, if necessary, and then stored in a computer memory.

Communication media typically embodies computer-readable instructions, data structures, program modules or other data in a modulated data signal such as a carrier wave or other transport mechanism and includes any information delivery media. The term "modulated data signal" can be defined as a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above-mentioned should also be included within the scope of computer-readable media.

When the subject matter is embodied in the general context of computer-executable instructions, the embodiment may comprise program modules, executed by one or more systems, computers, or other devices. Generally, program modules include routines, programs, objects, components, data structures, and the like, that perform particular tasks or implement particular abstract data types. Typically, the functionality of the program modules may be combined or distributed as desired in various embodiments.

Recitation of ranges of values herein are merely intended to serve as a shorthand method of referring individually to each separate value falling within the range, unless otherwise indicated herein, and each separate value is incorporated into the specification as if it were individually recited herein. Therefore, any given numerical range shall include whole and fractions of numbers within the range. For example, the range "1 to 10" shall be interpreted to specifically include whole numbers between 1 and 10 (e.g., 1, 2, 3, . . . 9) and non-whole numbers (e.g., 1.1, 1.2, . . . 1.9).

Although process (or method) steps may be described or claimed in a particular sequential order, such processes may be configured to work in different orders. In other words, any sequence or order of steps that may be explicitly described or claimed does not necessarily indicate a requirement that the steps be performed in that order unless specifically indicated. Further, some steps may be performed simultaneously despite being described or implied as occurring non-simultaneously (e.g., because one step is described after the other step) unless specifically indicated. Where a process is described in an embodiment the process may operate without any user intervention. Steps could be added or removed from the processes illustratively described herein.

For the purpose of clarification, to the extent that the description herein does not explicitly state that certain described portions are computer implemented or are carried out using computers, it would be understood to those of ordinary in the skill in the art from the specification that a computer implemented configuration is contemplated.

Recitation of ranges of values herein are merely intended to serve as a shorthand method of referring individually to each separate value falling within the range, unless otherwise indicated herein, and each separate value is incorporated into the specification as if it were individually recited herein. Therefore, any given numerical range shall include whole and fractions of numbers within the range. For example, the range "1 to 10" shall be interpreted to specifically include whole numbers between 1 and 10 (e.g., 1, 2, 3, . . . 9) and non-whole numbers (e.g., 1.1, 1.2, . . . 1.9).

In general, the use of "may" or "can" indicates a particular aspect of the present disclosure, but the technology herein is not limited to this one particular aspect.

It will be understood by those of ordinary skill in the art that described interfaces, components, or modules are related to descriptions herein when the descriptions are directed to the same or related features of the interface, component, or module.

Systems and methods described herein are particularly suited problems in this field of study. However, the terms and expressions which have been employed in the specification are used as terms of description and not of limitations, there is no intention in the use of such terms and expressions to exclude any equivalents of the features shown and described or portions thereof, but it is recognized that various modifications are possible within the scope of the claims to the disclosure.

Alzheimer's disease, like other chronic illnesses, is an age-associated imbalance that features many underlying mechanisms, and many of these biological mechanisms may need to be addressed therapeutically for clinical efficacy. For example, the association of Alzheimer's disease with low vitamin D intake, coupled with the neuroprotective effects of vitamin D, suggest that optimizing vitamin D serum concentration may be required for effective therapeutic response. Similarly combining beta-secretase (BACE) inhibition with a tau phosphorylation inhibitor may turn out to be preferable to the use of either alone.

Just as for other chronic illnesses such as cardiovascular disease, prevention and pre-symptomatic treatment are preferable to treatment later in the pathogenic process. Indeed, since Alzheimer's disease is a multi-prionic disease, more extensive combinations of therapeutics may be required late in the disease process than early. For example, prevention may not require a tau-phosphorylation inhibitor, whereas an effective therapy of Alzheimer's disease may require such an inhibitor.

Rather than focus on monotherapeutics, the system described herein involves systems of therapeutics, which include both pharmacological and non-pharmacological components. For example, if synaptic reconstruction and maintenance form parts of an effective therapy for Alzheimer's disease, then multiple biological mechanisms may require normalization, enhancement, or administration. Examples of these underlying biological mechanisms include, but are not limited to: minimizing inflammation, activating autophagy (periodically, perhaps), normalizing neurotrophic factors, reducing stress, inhibiting amyloid beta oligomerization, increasing amyloid beta clearance, reducing ApoE e4-mediated signals, reducing tau phosphorylation, blocking prionic tau amplification, reversing memory loss, restoring cholinergic neurotransmission and restoring overall network balance. Assessing the status of these biological mechanisms involves quantifying and observing hormonal balance, vitamin D (25-hydroxy), C-reactive protein (and other inflammation-related markers), homocysteine, sleep and melatonin, citicoline (citidine-5-diphosphocoline), specific antioxidants, diet (including intermittent fasting, avoidance of high-glycemic-index foods and saturated fats, etc.), exercise, stress, omega-3 fatty acids, and resolvins. The interventions of which such a system is comprised have already been shown to exert modest effects (trends that often have not reached statistical significance) on Alzheimer's disease or animal models of Alzheimer's disease. An interesting consequence of such a therapeutic system approach is that it may allow drug candidates that failed in monotherapeutic clinical trials to demonstrate beneficial effects when used as part of the system.

So, rather than a single therapy approach to treating dementia-related diseases such as Alzheimer's disease, systems and methods according to the present disclosure focus not necessarily on addressing a single underlying biological mechanism, but addressing the status of multiple underlying biological mechanisms at the same time. A set of goals, which are not necessarily orthogonal to one another, is identified to be addressed in a time period. The therapies involved to address multiple underlying biological mechanisms together involve overlap, contradiction, crosstalk, and prioritization, resulting in complexity in achieving them simultaneously. For these reasons, only through utilization of complex computing systems can therapy plans that consider the various biological mechanisms.

Combination of therapies, personalized to each person, with an order of magnitude of more components, may be implemented. As such, therapy plan or treatment plan may include a series of therapy actions for a participant. The level of involvement of each therapy action may increase with time if movement in the values of biological mechanism are not changing according to the probability models.

Embodiments of the present disclosure rely on dozens of biological mechanisms. For any person, each of these underlying biological mechanisms is in a certain state. Some of the states may be "just fine"—that is, measurements related to variables that correspond to a given mechanism lie within the recommended target range for the disease, and nothing is recommended to be changed at this time. Others may be in poor condition, and are thus the most dire, the ones to focus on first. Addressing the dozens of underlying biological mechanisms that lead to fulfilling the goals, that is, bringing the data variables associated with each mechanism into the recommended target range for the disease, is what brings about the reduction and reversal of the effects of Alzheimer's disease.

Examples of input fields may include:
1. Patient
   a. Name
   b. Date/Time of Birth
   c. Gender
   d. Identification Number
   e. Identification Number Type
   f. Address/Phone
2. Problem List
   a. Type
   b. ICD Code
   c. Patient Problem
   d. Status
   e. Date Diagnosed
   f. Diagnosed By
3. Medication List
   a. RxNorm Code
   b. Product
   c. Generic Name
   d. Brand Name
   e. Strength
   f. Dose
   g. Route
   h. Frequency
   i. Date Started
   j. Status
   k. Date Ended
   l. Indication
   m. Prescribed By
   n. Quantity
   o. Refills
   p. Comments
4. Medication Allergy List
   a. Type
   b. SNOMED Code
   c. Medication/Agent
   d. Date Recorded
5. Diagnostic Test Results
   a. Type
   b. LOINC Code
   c. Test (Normal Range)
   d. Result
   e. Date Performed
   f. Indication
   g. Requested By
   h. Comments
6. Procedure List
   a. Type
   b. ICD Code
   c. Procedure
   d. Status
   e. Date Performed
7. Vitals
   a. Temperature
   b. Blood Pressure
   c. Pulse
   d. Respiratory Rate
   e. Body Weight
   f. Body Height
   g. BMI
   h. Girth
   i. SpO2 level j. Date Recorded
k. Comments
8. Demographics
a. Gender
b. Age
c. Racial Category
d. Ethnic Category
e. Education Group
f. Preferred Written Language
g. LP Consent
h. Date Recorded
i. Comments
9. Cognitive Status
a. Type
b. Code
c. Test
d. Report
e. Date Observed
f. Date Recorded
g. Status
h. Comments
10. Family Medical History
a. Type
b. Relation
c. Code
d. Test
e. Report
f. Date Recorded
g. Status
h. Comments
11. Daily Activity Status
a. Type
b. Code
c. Activity
d. Report
e. Date Recorded
f. Status
g. Comments
12. Genomic Summary
a. Type
b. Code
c. Test
d. Results
e. Date Performed
f. Comments
13. Allergies
a. Allergen
b. Reaction
c. Date Recorded
d. Status
e. Comments
14. Immunizations
a. Type
b. Code
c. Immunization
d. Date Performed
e. Comments Certain input values can have a freshness associated with their data. For example, gender, genome (including ethnicity), height, historical personal history, traumas, allergies, and family history rarely change. Some values change predictably and slowly, such as a person's exact age. Some values decline with age, although not always predictably, such as eyesight, hearing, skin, hair, speed, muscle agility, and strength. In female participants, menopause becomes a value to consider with age. Some values change slowly, but not predictably, such as features identified in brain imaging, biomarkers identified in cerebrospinal fluid (CSF), cognitive capabilities, EEG, recent personal history, acute illnesses and traumas, chronic illnesses, allergies, list of medications, marital status, and pregnancies, recent family history such as chronic illnesses and allergies in the family. Some values change from day to day, but don't swing too wildly, such as weight, BMI, most blood serum and metabolomic test results, most urine tests, bowels, sleep, diet, and exercise. Some values can vary wildly from moment to moment, such as blood pressure, body temperature, insulin status, respiratory rate, and pain.

With respect to what to do about the principally-affected biological mechanisms, the current condition of the person is assessed in specific areas pertinent to the biological mechanisms related to the disease, to propose a set of prioritized interventions. The assessment information comes from a variety of sources for each person: medical histories, sequencing of their genome, blood tests, cognitive evaluations, and so on. A genomic assessment that shows a mutation indicating a strong likelihood for early-onset Alzheimer's disease will lead down a different path than for a person lacking that mutation. This collection of assessment information can be staged and directed, so not all tests or assessments are recommended with the same priority or urgency for each person. A broad set of assessment values (e.g., the contents of their genome, the results of their most recent cognitive evaluation, the homocysteine level in their bloodstream, their history of brain traumas) serve as input to a rules engine. The rules engine is designed to 1) describe the condition of the person—their diagnosis and prognosis, and 2) recommend what should occur next. Recommendations include best-practice therapies for addressing the goals: prescriptions, non-prescription, dietary changes, behavioral changes, even recommendations to get additional tests or information about medical experiences. Not only are a person's current test values used as input, but their entire history of inputs is used (as these can illustrate trends, effects, or correlations). The output of the engine serves as another input. Inputs from family members can also be used. Input across the entire population is used. The rules engine is complex, learns, has feedback loops, and creates output tailored to a person and their therapy team—and its output changes over time, as more input is received.

The steps to addressing the principally-affected biological mechanisms influence what the intervention components of the Alzheimer's therapy will be. Those interventions are personalized to each person's current condition, and they can change over time as the goals are addressed. Again, this is not a situation in which a single combination is identified and used. The number of intervention components for dementia-related diseases, such as Alzheimer's disease, is not one size fits all—it changes, by individual person, over time—and thus requires a big-data, analytical software solution.

The system can solve different technical problems that may have existed. For example, the system receives multiple streams of data from disparate sources that are received in multiple different formats. The system processes and analyzes each stream of data. The processed data is compounded and analyzed so that meaningful data for the prevention and changing the progression of dementia-related diseases when all of the data is utilized in combination, as deemed relevant for each person and situation. The system uses localized data received from the person and feedback of the system to provide an extra level of more accurate and updated therapy plans for each person. Feedback data is created by the system each time a therapy plan has been determined and also when progress or lack of progress of a person over a period of time will also contribute to feedback data. The system also provides seamless networking of data across many different systems and equipment, such as doctor's offices, hospitals; different medical devices and equipment; and input from caregivers, person, doctor, etc.

The system also provides the functionality to easily and seamlessly insert new information, components, or units. For example, the system provides the ability to easily insert a new medication or non-medication treatment into the system as another potential recommendation or therapy. The new medication would include information that helps recommend or suggest the medication based on the data determined about the participant, such as side effects, treatment benefits, conflicts with other medications or treatments, etc. The system may also easily insert other new components or information, such as new therapies, treatments, recommendations, medical tests, etc. The system also provides the functionality to determine the synergy between components and data through each iteration, feedback and the processing of any or all of the data.

An adaptive medical system that can update its operations automatically and track individuals to provide a proactive and accurate diagnostic state and also update and formulate treatment plans dynamically provides a more robust and valuable system. In some existing systems, clinical evaluations of data before use are always required.

The system can determine an appropriate target(s) (mechanism to target) based on the data, and use analytics and/or preprocessed analysis to identify treatments or therapies that have related performance characteristics that together form a combination or set that is optimal in general or optimal (highly effective) relative to other treatments (an intersecting set for a particular person or in general). This avoids less efficacious monotherapies and dynamically adjusts to have a better probability of success.

Aspects of the present disclosure can focus on a technique in which a significantly sized set of biological mechanisms are predetermined and the system operates to identify biological mechanisms that are out of balance and to correct the totality of out of balance mechanisms by way of the most effective path such that through sequential treatments each correct or improve at least one mechanism until the objective of adjusting all or substantially all of the mechanisms that are out of balance is accomplished. The system can identify treatment combinations that may have a higher combination success and can address and take into account personal information, drug interactions, and other factors. An aggregated solution can be applied to effectively treat dementia-related diseases. Preliminary research and analysis has shown that the application of the system to individuals results in effective results, such as curing Alzheimer's disease and/or changing the progression of cognitive decline associated with a dementia-related disease.

As described above, a computer or computer system with network connections and data storage implement features and embodiments of the present disclosure. The computer or computer system can communicate and interact with other devices to receive data or information, authorize or authenticate individual people, process and report current recommendations and/or priorities to end devices, or provide other functionality, tools, or interactions. Referring to FIG. 1, computer system 1 can include a display interface 2 that forwards graphics, text, and other data from the communication infrastructure 6 (or from a frame buffer not shown) for display on the display unit 30. As such, the computer system can generate signals or control the generation and display of graphics, GUI, other visuals or related interactivity on an attached display or a remote computer system (e.g., a PC client through a web browser). Computer system 1 also includes a main memory 8, preferably random access memory (RAM), and may also include a secondary memory 10. The secondary memory 10 may include, for example, a hard disk drive 12 and/or a removable storage drive 14, representing a floppy disk drive, a magnetic tape drive, an optical disk drive, etc. The removable storage drive 14 reads from and/or writes to a removable storage unit 18 in a well-known manner. Removable storage unit 18, represents a floppy disk, magnetic tape, optical disk, etc., which is read by and written to removable storage drive 14. As will be appreciated, the removable storage unit 18 includes a computer usable storage medium having stored therein computer software and/or data.

In alternative embodiments, secondary memory 10 may include other similar devices for allowing computer programs or other instructions to be loaded into computer system 1. Such devices may include, for example, a removable storage unit 22 and an interface 20. Examples of such may include a program cartridge and cartridge interface (such as that found in video game devices), a removable memory chip (such as an erasable programmable read-only memory (EPROM), or programmable read-only memory (PROM)) and associated socket, and other removable storage units 22 and interfaces 20, which allow software and data to be transferred from the removable storage unit 22 to computer system 1.

Computer system 1 may also include a communications interface 24. Communications interface 24 allows software and data to be transferred between computer system 1 and external devices or systems. Examples of communications interface 24 may include a modem, a network interface (such as an Ethernet card), a communications port, a Personal Computer Memory Card International Association (PCMCIA) slot and card, etc. Software and data transferred via communications interface 24 are in the form of signals 28, which may be electronic, electromagnetic, optical or other signals capable of being received by communications interface 24. These signals 28 are provided to communications interface 24 via a communications path (e.g., channel) 26. This path 26 carries signals 28 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 14, a hard disk installed in hard disk drive 12, and signals 28. These computer program products provide software to the computer system 1.

The present disclosure may also include a network communication connection that provides for communication between the different components of the system, as well as components that may be external to the system. For example, the diagnostic system of the present disclosure may be in communication with a doctor's office, hospitals, and mobile devices. A doctor's office or a hospital may have multiple devices that are capable of communicating with the diagnostic system. For example, different diagnostic tools within a doctor's office or hospital, such as magnetic resonance imaging (MRI) machines, and also mobile or desktop computers may communicate and provide data automatically to the diagnostic system of the present disclosure through a network communications connection. A participant or user of the system may be able to communicate with the diagnostic system through a mobile device, such as a smart phone, tablet, glucometer, or fitness tracker, or a personal computer through a network communications connection. The connection may be over the Internet or through some other remote connections means. The devices connecting to the diagnostic system over the network communications connection may include remote computers. These remote computers may be any kind of computing device that is remotely located from the diagnostic system that is capable of electronically communicating with the diagnostic system. Computer programs (also referred to as computer control logic) are stored in main memory 8 and/or secondary memory 10. Computer programs may also be received via communications interface 24. Such computer programs, when executed, enable the computer system 1 to perform the features of embodiments of the present disclosure, as discussed herein. In particular, the computer programs, when executed, enable the processor 4 to perform such features. Accordingly, such computer programs represent controllers of the computer system 1.

In an embodiment where the disclosure is implemented using software, the software may be stored in a computer program product and loaded into computer system 1 using removable storage drive 14, hard drive 12, or communications interface 24. The control logic (software), when executed by the processor 4, causes the processor 4 to perform the functions or features described herein. Data as part of one or more databases or storage structures can also be part of the computer system and work together with the other components to provide new tools operations, systems, or features to managers and participants. In another embodiment, the features are implemented primarily in hardware using, for example, hardware components, such as application specific integrated circuits (ASICs). Implementation of the hardware state machine so as to perform the functions described herein will be apparent to persons skilled in the relevant art(s). In yet another embodiment, a combination of both hardware and software can be used.

A computer system can be used that comprises one or more computers or computer systems. Depending on the arrangement, a display unit that is attached to the computer system (e.g., using a VGA cable) or to one of the computer systems may not be necessary. A computer system and a computer are used interchangeably throughout the description.

As shown in FIG. 1, embodiments of the present disclosure may be implemented using hardware, software, or a combination thereof, and may be implemented in one or more computer systems or other processing systems.

Now referring to FIG. 2, which illustrates a system diagram of components for a comprehensive and dynamic tool for therapies to prevent and change the progression of dementia-related diseases. System 200 includes a user interface 202, a diagnostic system 204, a protocol rule engine 206, a user data store 208, a physician data store 210, and a therapy data store 212. System 200 is not limited to only these components. It should also be appreciated that any of these components may be components that are separated or together and that are co-located or remotely located. The system 200 is not limited to only the storage of the three data stores illustrated. System 200 may also receive or store data from other sources.

User interface 202 may provide the interface between diagnostic system and the user. The user may be any number of individual people, such as the participant, their caregivers, doctor, the staff at a doctor's office or any individual person, that is, the person's therapy team. The user interface 202 may provide forms and questions for the person's therapy team to answer so the person can be registered with the diagnostic system 204 and a profile created for them. The person's therapy team may also be given login information, such as a user ID and/or a password for access to specific profile information. Members of a person's therapy team may only be allowed to access only their specific profile information, but a doctor or staff at a doctor's office may be able to access multiple profile's that are associated with the doctor or doctor's office. In order to comply with HIPAA regulations and provide security of the information for individual people, the login access system may be encrypted and protected to prevent unauthorized access in many different ways.

Next, the diagnostic system 204 may retrieve data from an individual's electronic health record (EHR), which is also known as an electronic medical record (EMR). As computers have become more prevalent, most people have some health records that are electronic. Many health records at doctor's offices, hospitals, and insurance providers have already been converted into an electronic format. So, the diagnostic system 204 may receive any EHR information that is available for the individual person. Again, there might be requirements either from the system providing the EHR information and/or the diagnostic system 204 to provide a secure connection and authentication to prevent a breach of secure information. In order for the diagnostic system 204 to retrieve information about the right individual person, the member of the person's therapy team may provide detailed identification information about themselves or the person.

The type of information that may be available in an EHR may include, but is not limited to, health history, medical history, family history, primary provider, insurance, caregiver information, etc. Also, some information may not be available in an electronic format. So, if there are specific records that are important, but have not shown up in the EHR information, there are third-party companies that provide services that convert medical records into the proper EHR format. The diagnostic system 204 is capable of communicating with such third party companies to receive such information. When available or important information is received for the individual person, a profile is created.

The user interface 202 may present the person's therapy team with a number of questions to gather pertinent information about the individual person. The diagnostic system 204 may have thousands of questions that they could ask about a person. So the diagnostic system uses the already-received profile information to prioritize questions to ask the person's therapy team to get the information about the individual person that best directs the therapy recommendations. Examples of some of the questions may be, "Do you smoke? How much alcohol do you drink? How much sleep do you get, on average?" Each answer to the question may also suggest further follow-up questions. For example, if the question "Do you smoke?" receives the answer "Yes," the diagnostic system 204 may then be prompted to ask another question, such as "How much tobacco do you consume each day, on average?" Each answer to a question will provide the system with more relevant information and help decide the question that best directs the therapy recommendations. The questions may also be asked at a doctor's office by a doctor or staff member, such as a nurse or physician's assistant—that is, to any appropriate member of the person's therapy team.

Next, the diagnostic system 204 determines whether the individual person is a dementia-related disease candidate. There are different stages that a person may go through in a dementia-related disease. The seven stages described here correspond to the Reisberg Scale, also known as the Global Deterioration Scale, used to quantify the progression of Alzheimer's disease. These stages are determined based on the profile information about the person.

Stage 1 is usually considered no impairment. At this stage, a person does not experience any memory problems and an interview with a medical professional does not show any evidence of dementia. Anyone not in stage 1 is considered a dementia-related disease candidate for the diagnostic system (204). A regular person may be asymptomatic, but there are many behavioral changes most people can make to help prevent future problems.

Stage 2 is considered a very mild cognitive decline. At this stage, it may be normal age-related changes or the earliest signs of a dementia-related disease. A person may feel as if he or she is having memory lapses, by forgetting familiar words or the location of everyday objects. But, often no symptoms of early dementia can be detected during a medical examination or by friends, family or co-workers.

Stage 3 is defined as a mild cognitive decline. At this stage, early-stage dementia-related diseases may be diagnosed in some but not all people at this stage. Friends, family, and/or co-workers may begin to notice difficulties. During a detailed medical interview, doctors may be able to detect problems in memory or concentration. Common stage 3 difficulties may include noticeable problems coming up with the right word or name, trouble remembering names when introduced to new people, having noticeably greater difficult performing tasks in social or work settings, forgetting material that one has just read, losing or misplacing a valuable object and/or increasing trouble with planning or organizing. A person who is assessed as being in stage 2 or 3 does not always have a dementia-related disease. For example, other external issues may cause cognitive impairment, such as too much exposure to lead or mercury, side effects of certain drugs, concussions, etc.

Stage 4 is defined as a moderate cognitive decline. At this stage, it is usually considered mild or early-stage of a dementia-related disease. A careful medical interview should be able to determine these symptoms in a person in several areas: forgetfulness of recent events; impaired ability to perform challenging mental arithmetic (e.g., counting backward from 100 by 7s); greater difficulty performing complex tasks (e.g., planning dinner for guests, paying bills or managing finances); forgetfulness about one's own personal history; and/or becoming moody or withdrawn, especially in socially or mentally challenging situations.

Stage 5 is defined as a moderately-severe cognitive decline. At this stage, a person is usually diagnosed with moderate or a mid-stage dementia-related disease. The person may experience noticeable gaps in memory and thinking, and they may begin to require assistance accomplishing day-to-day activities. This stage may include these symptoms: be unable to recall their own address or telephone number, or the high school or college from which they graduated; become confused about where they are or what day it is; have trouble with less challenging mental arithmetic (e.g., counting backward from 40 by subtracting 4s or from 20 by 2s); needs help choosing proper clothing for the season or the occasion; still remembers significant details about themselves and their family; and/or still requires no assistance with eating or using the bathroom.

Stage 6 is defined as a severe cognitive decline or a mid-stage dementia-related disease. The person's memory continues to worsen, personality changes happen and the person may need extensive help with daily activities. At this stage, a person may lose awareness of recent experiences as well as of their surroundings; remembers their own name but has difficulty with their personal history; distinguishes familiar and unfamiliar faces but may have trouble remembering the name of a spouse or caregiver; needs help dressing properly; makes mistakes, such as putting pajamas over daytime clothes or shoes on the wrong feet; experiences major changes in sleep patterns (e.g., sleeping during the day and becoming restless at night); needs help handing details of going to the bathroom; exhibits compulsive or repetitive behavior (e.g., hand-wringing or tissue shredding); and/or tends to wander or become lost.

Stage 7 is defined as a very severe cognitive decline or late-stage dementia-related disease. In the final stages of these diseases, people lose their ability to respond to their environment, to carry on a conversation and eventually, to control movement. They may still say words or phrases. At this stage, a person needs help with much of their daily personal care, including eating and going to the bathroom. They may also lose their ability to smile, to sit without support and to hold their heads up. Reflexes may become abnormal, muscles grow rigid and swallowing is impaired.

It is determined that a person is a dementia-related disease candidate or not based on the profile information. If it is determined that someone is not a candidate, the person may still receive a list of recommendations that they can implement in their daily life to either improve certain factors of their health or help prevent a dementia-related disease in the future. For example, the recommendations may include, but are not limited to, get at least eight hours of sleep, exercise more, eat healthier, etc.

If it is determined that a person is a dementia-related disease candidate, then usually one of two things may happen. If the person's situation is severe, the diagnostic system 204 will recommend that the person follow up with a doctor soon. Most likely the person has a dementia-related disease, and appropriate therapies for reducing and reversing its progress should be initiated. Going through this process as a preliminary step prior to seeing a physician may provide the physician and the physician's staff with granular information that makes diagnosing and treating the individual more focused. If it is determined that the person's situation is severe, an early-onset diagnosis may be determined by either the diagnostic system 204 and/or the doctor. The diagnostic system 204 may then recommend getting a brain scan and/or a cerebrospinal fluid (CSF) test. CSF collection can be painful, but since the test measures the composition of fluid from the brain stem, it is informative as to the cognitive status of the brain.

If it is determined that a person is a dementia-related disease candidate, then the diagnostic system 204 may recommend that the person get a cognitive evaluation, which may be administered by a psychologist or physician. Examples of cognitive evaluations include the Mini-Mental State Examination (MMSE), the subtests that comprise the Repeatable Battery for the Assessment of Neuropsychological Status (RBANS), the Self-administered Gerocognitive Examination (SAGE), the Montreal Cognitive Assessment (MoCA), and the California Verbal Learning Test (CVLT). The cognitive evaluation may provide more information in combination with the profile information stored in the system that can give the diagnostic system 204 and/or the doctor more information for establishing a baseline. In addition to a cognitive evaluation, an interview with the individual's family, such as spouse, children or caregiver, may also be conducted. Both the cognitive evaluation and the interviews may provide more information that the doctor and/or the diagnostic system 204 may utilize to give insightful diagnosis and effective therapy. Once the cognitive evaluation and/or interviews have been conducted, a baseline diagnosis is determined. The cognitive evaluation and/or interviews may also be entered into the system by the person themselves, the doctor or transferred electronically as an EHR. The baseline diagnosis may also be determined by the diagnostic system 204 based on the profile information, cognitive evaluation and/or interviews.

After a baseline diagnosis, the doctor may request the person to specific blood serum or metabolomic testing. The normal blood test range is usually insufficient, and the doctor may recommend that other variables are measured, such as homocysteine and hormone levels. Once the blood test results are received, the results may be entered into the diagnostic system 204 by a member of the person's therapy team or automatically as an EHR.

Mild cognitive impairment (MCI) may be caused by issues other than a dementia-related disease, such as toxic metal levels in the bloodstream, a history of concussions or severe trauma, or side effects from other medications. After the blood test, the diagnostic system 204 may recommend the individual get a brain scan, such as a Pittsburgh compound B (PiB) scan, a magnetic resonance imaging scan (MRI), or a positron emission tomography (PET) scan. These scans may provide information about the person's brain functioning, composition, and structure, and show the change in these over time.

Next, the diagnostic system 204 may provide, based on the results of the PiB, MRI, and/or PET scan, insight into improved recommendations that might be gained by having the person's genome sequenced. The diagnostic system 204 may not require recent data results from each of these types of input to make the determination of whether an individual has MCI, but each test performed refined the confidence in the diagnosis and refines the recommendations for the next test and what information is being sought.

Accordingly, a computer system that manages therapy plans related to dementia-related diseases is provided. The system includes at least one computing device having computer executable instructions store thereon and a remote computing device having computer executable instructions store thereon. The executable instructions are configured to receive user-associated data for participants including an image of a participant's anatomical feature or other characteristic of a participant's anatomical feature. The instructions are further configured to receive therapy-associated data for participants including individual therapy plans that specify corresponding individual ones of the biological mechanisms that each individual therapy targets to adjust a physiological state of the corresponding biological mechanisms. The therapy-associated data contains variations found in the individual therapy's effect on the corresponding target biological mechanisms as a function of the personal background data and contains data quantifying a probability of success of the therapy. The instructions generate an expected adjustment of individual biological mechanisms resulting from particular combinations of the therapies and a probability reflecting the likelihood of reaching those therapy results and receive diagnostic and testing data associated with the participant after the participant has undergone treatment according to the therapy plan from the at least one computing device to generate values associated with biological mechanisms in the participants based on the received diagnostic and testing data. The diagnostic and testing data including an updated image of the participant's anatomical feature. In response to the generated values, dynamically adjust the therapy plan to a modified therapy plan when the generated values are within a recommended range, wherein the dynamically adjusting comprises using the received diagnostic and testing data to generate the adjusted therapy plan.

The remote computing device monitors the image of the participant's anatomical feature, where the anatomical feature is the brain and the remote computing device monitors the image for changes in predefined areas of the participant's brain. In one or more embodiments, the remote computing device is configured to determine a shrinkage rate of the predefined area. In one or more embodiments, the remote computing device is configured to determine a change in the shrinkage rate of the predefined area. In one or more embodiments, the remote computing device is configured to receive data related to shrinkage rate and reverse shrinkage rate from a third party. In one or more embodiments, the computer system includes at least one of a magnetic resonance imaging device, CT scan, PET scan, EEG scan, magnetoencephalography (MEG) neuroimaging, and near-infrared spectroscopy (NIRS) neuroimaging. In one or more embodiments, the predetermined area includes multiple locations of the participant's brain. In one or more embodiments, the remote computing device is configured to compare the image of the brain with an expected result based on one or more characteristics of the participant, including age and gender.

A recommended therapy plan is created for the person using many different sources of information. A therapy plan may include one or more therapies. Examples of therapies may include medications, nutraceuticals, changes in daily behaviors, dietary changes, and non-pharmacological components, etc. Information provided in the profile and any test that has been performed is utilized, as well as information gleaned from the general population. Further, the system 200 includes a protocol rules engine 206 that communicates between different data stores 208, 210, 212 and the diagnostic system 204. It is proposed that there are dozens of underlying biological mechanisms to be addressed in Alzheimer's disease, but additional biological mechanisms pertinent to influencing the course of the disease are likely to be discovered. Each of these biological mechanisms has a significance or importance that differs for each individual person. It would be overwhelming for a person's therapy to try to adjust the operation of dozens of biological mechanisms simultaneously. For example, it might be discovered that a person has ten biological mechanisms of high priority to be addressed, that is measurements of data elements related to those ten biological mechanisms are outside of the recommended target range for that disease. It may be behaviorally difficult for that person to make changes to their routine and life to make improvements in all ten underlying biological mechanisms at once. It is also important to mention that some of the system's recommendations may improve multiple biological mechanisms. For example, improving nightly sleep may help to improve the measurements for five of the underlying biological mechanisms.

The diagnostic system 204 and the protocol rules engine 206 determine which biological mechanisms to focus on first, using a prioritized list of the most effective recommendations. The prioritized list is compiled using the individual's profile information, medical tests and history, as well as historical information from other individuals either in the same situation or similar situation. The user data store 208 may include all relevant user or individual information, such as profile information, test data, behavioral data, dietary summaries, etc. The physician data store 210 may include information, such as medical records, research, articles, etc. The therapy data store 212 may include information, such as how to recommend effective therapy plans at various assessed conditions. It may also include information about acceptable ranges for test data. The therapy data store 212 helps take the information from other sources and provides a rubric or template against which to measure the information. For example, an individual may have a low-density lipoprotein (LDL) cholesterol result. There is a range in which LDL is high, normal, or low, or dangerously high or low. This is usually used to indicate how this affects someone's cardiovascular status. The acceptable levels of LDL cholesterol for effective cardiovascular improvements may differ from acceptable levels for providing information about a current or future dementia-related disease diagnosis. As described below, the diagnostic system 204 also provides recommendations for medication and dosage. Having information such as a person's LDL cholesterol level, among other information, will help the diagnostic system 204 to provide accurate and helpful recommendations.

As the information is processed, the state of all of the underlying biological mechanisms pertinent to the disease is scored. Once the mechanisms are scored, then they are prioritized by their influence on the disease. Some of these biological mechanisms may be most significantly operating out of range or most feasible to improve, etc. The prioritized biological mechanisms (or a subset of the mechanisms) may become a targeted list of mechanisms for the person's therapy team and the diagnostic system to concentrate on for the coming time period. For example, lack of sleep may affect five different mechanisms. The prioritized list is then used to create a recommended therapy plan for the person. Their doctor and other members of the person's therapy team may review the therapy plan prior to the individual receiving the plan. The system provides a thorough and comprehensive analysis to aid in the diagnosis and prognosis for the doctor. Once the doctor either signs off on the compiled plan or makes adjustments (which are also recorded and noted for future use), the plan is presented to the person's wider therapy team.

It is then up to the person's therapy team (the person themselves or maybe in combination with family, caregivers, therapists, and so on) to implement the recommendations for a specified amount of time period, such as three to six months. Examples of recommendations may include, but are not limited to, new medications, increase/decrease dosage of current medications, more sleep, more exercise, altered dietary components, etc. After the initial time period has lapsed, the person returns to the doctor to get follow-up tests. These may start with selected blood and urine tests to gauge any progress that has been made by implementing the recommendations over a period of time. The diagnostic system 204 and/or the doctor may review the results of the follow-up blood test to determine if the test results are sufficient to measure progress or may order additional test, such as an EEG, brain scans, etc. The tests may be compared to the past tests to show any progress. Depending on any progress that is noticed in the received test results, the individual's disease-related biological mechanisms are scored again. Depending on the new score, a new prioritized list of recommendations is determined. In one embodiment, the disease-related biological mechanisms are only updated when new information is provided. In another embodiment, the mechanisms may be periodically monitored and scored. The monitoring may also be automatic. The system may periodically receive data about a person and that may trigger a rescoring of the mechanisms. The mechanisms may be rescored based on a periodic factor, such as every month, three months, six months, etc. The mechanisms may also be rescored manually as requested by a person, such as a doctor, the person themselves, the person's therapy team, etc.

Also, information such as past trial data may be used to determine or predict improvements in certain mechanisms. The doctor reviews the recommendations and provides feedback to the diagnostic system 204. Information provided from the first recommendation based on what the doctor agreed with and the results over the time period will also be taken into consideration in providing recommendations for this person and future people. The process should go on indefinitely throughout a person's life. So, a person may come in for an appointment and tests, and then may be instructed to come back after a specific period of time to retake any tests and check for improvement, decline, or abnormalities. For example, the time period may be distanced relatively shortly apart, but far enough apart to see some improvement measurements associated with the targeted biological mechanism, such as three, six or nine months, but the present disclosure is not only limited to these time periods.

Now referring to FIG. 3, which is a schematic flow diagram of the process (300) of evaluating a person's data to create a raw list of recommendations and priorities. When a person's therapy team first logs into the system and starts to enter information, the entered information is evaluated or processed. The processing steps below may be performed any in order, in combination or simultaneously. The person's demographic information, such as age, gender, body mass, etc., is evaluated (302). The individual's vital information is also evaluated (304). Next, the individual's personal medical history is evaluated (306). The individual's personal medical history may include, but not limited to, a medication list, medication allergies, immunizations and vaccinations, and/or a list of past medical procedures. The individual's family history is evaluated (308). The family history may be important if there is any family history of dementia-related disease, or of other symptoms or diseases that may complicate recommended therapies. Next, the genomic data or genetic information is evaluated (310). This information may provide insight as to whether an individual has a predisposition for a dementia-related disease, has a predisposition for other chronic diseases that may complicate diagnoses or therapies, or may indicate the likelihood of certain medications or therapies to have amplified, reduced, or contra-indicated results.

Next, information such as biomarkers, images, and scans are evaluated (312). Then an electroencephalography (EEG) recording or measurement is evaluated (314). It should also be noted that not all people will have recent information in these areas, and their diagnosis to this point may not require this additional information. The system provides for handling all of the information, but it is not required to have every piece of data in order to provide meaningful results. Next, bio-specimen test data is evaluated (316). Bio-specimens may include, but are not limited to, blood work, cerebrospinal fluid (CSF) results, and urine test results. Next, behavioral history data is evaluated (318). Behavioral history data may include observations related to sleep, exercise, stress, dietary habits, alcohol use, tobacco use, and recreational drug use. The behavioral data may be received from simple queries, or gathered via sensor-based or other measurement devices that a person wears that communicates or downloads information to the system, such as vital signs, sleep patterns, movement and exercise patterns, dietary habits, glucose levels, and so on (such devices are known to people pursuing the field of "quantified self"). Accordingly, any wearable device capable of detecting or determining one or more data sets that may be utilized by the one or more methods and systems disclosed herein may be provided. The wearable device may also be configured, in communication with the computing device, to determine compliance with one or more steps or treatments in the therapy plans. For example, if a participant is instructed to get eight hours of sleep per night, the wearable device may be configured to detect movement indicative of sleeping or movement not indicative of sleeping. In instances of non-compliance, intervening measures may be ordered. This further ensures the viability of data related to the therapy plans so that false readings for values of biological mechanisms are not provided for a participant that is supposed to be receiving a given treatment plan but is not complying.

Next, any previous recommendation data may be evaluated (320). This would be necessary if the person has previously received recommendations from the system and/or a physician. (This is an optional step if this is the first time logging into the system.) Next, any cognitive evaluations and/or test results are evaluated (322). Based on any combination of the above evaluations, a raw list of recommendations and priorities is generated for the person (324).

Now referring to FIG. 4, which is a schematic flow diagram of a person's process 400 of the comprehensive and dynamic tool for therapies to prevent and change the progression of dementia-related diseases. Process 400 may also be implemented with a therapy insertion module that receives new therapy information (such as new recommendations) and seamlessly adds and incorporates the new data into the existing diagnostic system and updates any future or existing plans, if necessary. First, a person's profile is either registered or loaded into the diagnostic system (402). If it is the person's first time using the system, then the person would have to be registered and supply the system with at least some of the information mentioned above. Otherwise, the person has already been registered; a member of the person's therapy team logs in and the profile information is loaded. Next, the person's profile is evaluated based on profile information and history (404). Again, if this is the first time the person has been logged into the system, this is the first evaluation performed by the diagnostic system on the person's profile information. The evaluation determines the potential cognitive impairment of a person and determines if the person is a dementia-related disease candidate. If a member of the person's therapy team has previously used the system, then the previous evaluation performed on the profile is also loaded and re-evaluated based on any new information entered into the system, such as new test data, etc.

Next, the recommendations and priority list is reevaluated (406). If this is the person's first time to be logged into the system, then this step will create an initial recommendation and priority list based on the evaluation performed on the profile information and history. If this is not the person's first login, the diagnostic system will use previous recommendations and priority lists, compare those with any new information either from the profile or from other sources, and prepare a new recommendation and priority list for the person. The person's current status is also summarized (408). The summarization is based on the final recommendation and priority list and any new information or progress in the profile. The doctor may review the summarization and determine whether or not to use all of the recommendations or make any adjustments. Next, the current recommendations and/or prognosis are provided to the person's therapy team (410).

Now referring to FIG. 5, which is a schematic flow diagram of the process 500 of evaluating each data element in the system. Essentially, process 500 is a prioritization engine that regularly updates each data element that is stored in the system. A data element may be any piece of information that is stored in the system, such as any information about an individual person, doctor, test results, recommendations, statistics, etc. The process 500 helps determine the priority of data related to the specific data element. Process 500 may also be used to determine synergic data, which helps to determine the probability for each therapy on the recommendation or priority list. The synergic data helps to create synergy between the different therapies because each therapy is compared to other therapies to determine priorities and recommendations. The synergic data may include data from each new data element that is received about each person compounded with data that has already been received or determined. Therefore, each time new information is received a synergy or lack thereof may be determined between the updated information and what was previously known. The synergic data may include information from research, past successes and/or failures, etc. By compounding the data with each new update or new data element, the determination of a likelihood or probability becomes more accurate as more information is received. With more data points, the more tailored and accurate the recommendations and therapies become. Examples of the processes that help create and determine synergic data include processes 500, 600, 700 and 800. These processes are merely an example and are not intended to be an exhaustive list. For example, step 504 in FIG. 5 may be part of generating synergic data.

First, the diagnostic system determines if a data element is missing (502). If it is determined that the particular data element is missing, then a recommendation to ask the person's therapy team about this data element is added to a recommendation list (504). But, there may be hundreds of recommendations in the list. That is where the prioritization determination is important, because this process communicates with the rest of the system to determine whether or not knowing the information associated with this data element is a high priority or not. Once a data element has been added to the recommendation list, the process ends (508) and the next data element is processed. The recommendation list also determines which questions are asked to the person's therapy team; these questions are designed to refine the list of recommendations for this individual. The questions themselves are added to the recommendations list, along with calculated priority for each question. For example, a question about the onset of menopause may be deemed to have higher priority than a request to obtain a more recent hemoglobin A1c blood serum test result. If it is determined that the element is not missing, then it is determined whether the element has been stored past a certain threshold (506). The diagnostic system determines if the information stored in this data element is too old and thus no longer relevant or whether it has some strength of relevance. The system may create different data aging thresholds for different types of data elements. For example, CSF composition changes slowly, so it would be okay for a test to be 4 months old. But, a person's weight measurement or a blood test that is 4 months old may no longer reflect their current status well, and the collection of a more recent measurement would be recommended with an appropriate priority. If it is determined that the element is too old to have strength of relevance, then a request for an update to this data element may be added to the recommendation list (504) and the process ends (508). If the element is not determined to be too old, then it is next determined whether the data stored in the element is suspicious (510). Suspicious data may include, for example, that a person has gained 100 pounds in a month. The data is probably inaccurate because it is unlikely for an individual to gain 100 pounds in a month (for instance, it might be a typo, where the number "10" should have been entered instead). If it is determined that the information is suspicious, then a request for an updated value will also be added to the recommendation list (504) and the process ends (508).

If the element is not considered suspicious, the individual's data is assessed (512). The individual's data may include, but is not limited to, vitals, demographics, tests, genomics and/or other conditions. Next, it is determined from the individual's data whether or not to change the shape of the evaluation curve describing the handling of this particular data element (512). The evaluation curve for each data element describes the values that are optimal, normal, high or low (suggesting therapy), or dangerously high or low. Changes to the evaluation curve in the therapy database may reflect values that differ by age or gender or other variables related to the state of the person. Its shape may need to change when new data has been added to the system, and the system needs to determine how this new piece(s) of information affects the rest of the data and any results or recommendations. Using this process, the likelihoods and/or probabilities may be determined. Changes to an evaluation curve may affect the likelihood of future recommendations or therapies. Likelihoods and/or probabilities may include or use methodologies to determine an outcome of success, such as weighted values, statistics, etc. The likelihoods and probabilities may be based upon empirical data received from collections of journal articles, other scientific data collected by physicians, and based off of historical probabilities as determined by the system disclosed herein. The likelihoods and probabilities and data which is used to determine the same may be stored in any appropriately configured database in communication with the computing device disclosed herein. If it is determined that there does need to be a change in the evaluation curve, then the system will implement the update on the data (516). If there is no change necessary or after the change has been implemented, it needs to be determined whether the data value is at an optimal level for dementia-related diseases (514). If it is determined that the data element is at an optimal value for dementia-related diseases, the process ends (508).

One of the biological mechanisms underlying a dementia-related disease, such as Alzheimer's disease, deals with how the brain reacts to iron, copper, and zinc in the bloodstream. These metals differ from the toxic metals, such as mercury, chromium, and arsenic, which underlie another biological mechanism. Blood tests can readily measure what the levels of those metals are. One measurement is the ferritin level, which indicates the level of iron. Normal ferritin levels for the American population are described as: for men the level should measure between 18-270 nanograms per milliliter (ng/mL); women age 15 to 49, the level should measure between 12-156 ng/mL; above age 49, normal is considered 18-204 ng/mL; children 6 months to 15 years should measure between 7-140 ng/mL; babies 1 to 5 months should measure between 50-200 ng/mL; and newborns should measure between 25-200 ng/mL. These values may represent what is considered "normal," but does not consider Alzheimer's disease. A different range of values describes what the target range for good cognitive health. For example, a male with a ferritin value of 265 ng/mL might be considered within normal range for an overall purpose, but that value is too high for long-term cognitive health and thus, may have an increased risk of acquiring Alzheimer's disease or another dementia-related disease.

It can be observed that "normal" levels of ferritin vary by age and gender. If the algorithm or process of the present disclosure does not currently know age and/or gender, the process can still make a best guess and generate an initial curve based on distribution of gender by age, and then draw the curves for those across the entire population, e.g., how likely is it that the person is a 75-year-old female, etc. The process may start with a basic curve and, based on the more information that is received, adjust the curve to reflect the updated or new information. The state of other biological mechanisms may be more critical and may make recommendation to adjust one's ferritin level a low-priority recommendation.

For good cognitive health, the healthy range of serum ferritin lies between 20 and 80 ng/mL. Below 20 is a strong indicator of an iron deficiency, and a value above 80 suggests an iron surplus. The optimal range is between 40-60 ng/mL. The higher the number over 100, the worse the iron overload, with levels over 300 being particularly toxic. A high level of iron can amplify one of the mechanisms that underlie a dementia-related disease, such as Alzheimer's disease. Levels above 300 ng/mL have been seen to cause serious damage in nearly everyone that sustains those levels long term.

If the ferritin level is above the algorithm's normal range, therapies may include deferoxamine and chelation therapy. Recommended therapies may be tailored to the individual, cognizant of other priorities, disorders, medications, medication allergies, genetics, feasibility, and so on. If the ferritin level is too low, therapies include an iron-rich diet and iron supplements. But, low ferritin levels are not usually a driver behind dementia-related diseases.

Ongoing measurements of these three metal levels (ferritin, copper, and zinc) are one of the underlying biological mechanisms to be pursued. If none of the three measured values are above normal for the process expectations, then no additional recommendations are generated with respect to these metal levels. On the other hand, if a person gets blood tests four times a year and the metals measured in the bloodstream show an unfavorable upward trend (while still within normal ranges), the process may generate a recommendation to try to understand the undesirable trend. Similarly, the individual may have a medical history that includes low efficacy, adverse side effects, or interference from other medications. These may also be considered in generating the recommendations. Other biological mechanisms, if in far dire states, may make the adjustment of ferritin levels a low-priority recommendation. The ongoing measurements of these three metal levels (ferritin, copper, and zinc) are one of the underlying biological mechanisms to be pursued.

If it is determined that the value is not optimal, then the next step is to determine if the value is within a normal range (518). If it is determined that the value is within a normal range, the process ends (508). If it is determined that the value is lower than the normal range, then it needs to be determined if the value is low but still essentially at a safe level (520). If it is determined that it is at a low but safe level, then interventions based on the data element is added to the recommendation list but at a relatively low priority (524) and the process ends (508). If it is determined that the value is dangerously low (and thus not safe), then medical interventions based on the data element is added to the recommendation list but at a high priority (426) and the process ends (508). If it is determined the value is higher than the normal range, then it needs to be determined whether the value is high but still safe (522). If the value is determined to be high and safe, then the data element is added to the recommendation list but at a relatively low priority (524) and the process ends (508). If it is determined that the value of the date element is dangerously high and not safe, then the data element is added the recommendation list at a high priority (526) and the process ends (508). It should also be appreciated that the above process and any other process described herein may be dynamically or continuously updated as new data is received. In other words, the systems or features such as those that dynamically perform an operation, perform the operation automatically without requiring human review, confirmation, or intervention.

Example evaluation curves are illustrated with reference to FIGS. 10A and 10B, which show two evaluation curves for the same woman, at two different times in her life. FIG. 10A shows the reaction to the range of measured estradiol serum levels, at age 35. It is divided into 7 ranges on the x-axis. The optimal range for this participant is from 150 to 175 pg/mL, which can be seen in the top of the y-axis. Less than optimal, but not needing particular disclosure is the next span; on the low side, from 100 to 150, and on the high side, from 175 to 300. When values in these ranges are seen, they should be observed over time to see how they're trending.

Values in the range of 40 to 100 are too low, and suggest an intervention for managing low estradiol. Values in the range of 300 to 375 are too high, and suggest an intervention for managing high estradiol levels. Values less than 40 are far too low, and probably should be considered for immediate observation or hospitalization; similarly, for values higher that 375, although the interventions and what's being observed is quite different.

FIG. 10 B illustrates a curve at a later moment in the life of the woman, at age 62. The curve is vastly different, the target values for optimization or treatment are vastly different. The interventions may be vastly different. It's highly sensitive to small changes in small numbers.

These curves are not isolated; they're for the same woman. The top ones progress into the bottom one simply with the passage of time. There are an infinite number of curves, slightly different from these, that morph minute-by-minute through this person's life. Two curves, yet an infinite number of mappings simply when considering this third variable: time. But, many more factors than time can affect these, such as progesterone levels, a hysterectomy, diabetes, heart disease, BMI, chronically high stress levels, and so on. Each factor can deform the evaluation curves, in big ways or small, over short time periods and long ones.

Now referring to FIG. 6, which is a schematic flow diagram of the process 600 of reevaluating the list of recommendations for a person. Process 600 may be considered a second prioritization engine that takes the raw list of recommendations and priorities compiled from processes 300 and 500 and creates a more refined and narrowed list of recommendations and priorities. First, the raw list of recommendations and priorities is received (602) from process 300 of FIG. 3. The next set of steps can be done in any order, parallel or in sequence. The recommended diagnostic requests are evaluated (604). Out of the recommended diagnostic requests, each request is assessed (606) to determine the most efficient and effective order each request should be presented to the person's therapy team. The system may make a determination for each diagnostic request and then once each request has been assessed, the system will provide the prioritized diagnostic system to be part of an overall list of recommendations and priorities. Each separate list will be then compared against each other (608) for an overall refined list of recommendations and priorities (610). Then, the list of medications, supplements, nutraceuticals, or vitamins is evaluated (612). Each pharmacological component is assessed (614) and for each medication, the dosage is assessed (616). The process of assessing the medication (614) is further described in FIG. 7. The process of assessing the dosage (616) is further described in FIG. 8. After the dosages and medications are assessed and reprioritized among themselves, the list is added to be reevaluated at 608.

Next, the non-pharmacological components are evaluated (618) and each component is assessed 620. Examples of a non-pharmacological component might be: increase sleep, increase exercise duration or intensity, etc. The re-evaluated list of non-pharmacological components is then added to the overall list of recommendations (608). Then, the recommended dietary components are evaluated (622) and assessed (624). Examples of a dietary component might be increase daily consumption of fruit and vegetables, decrease red meat consumption, etc. After the list of dietary components is prioritized, they are also added to the overall recommendations list (608). After all of the evaluation and assessment steps, each individual list is compared against each other to determine across the entire list the prioritization order of each component within the list to be presented to the person's therapy team (608). After, the reprioritization of the overall list, a refined list of recommendations and priorities is generated (610).

The refined list of recommendations may be also considered a refined therapy plan that includes one or more therapies and/or recommendations. The refined therapy plan may be determined from the process described above with respect to FIG. 6 utilizing data elements, metadata, and/or person or user-related data. The diagnostic system uses that data to determine based on the person's information which therapies or recommendations to suggest or implement in combination with the synergic data.

Now referring to FIG. 7, which is a schematic flow diagram of the process (700) of assessing and updating a pharmacological recommendation. There is a list of medications received from the raw list of recommendations and priorities discussed in FIG. 6. Each medication on the recommendation list is assessed and prioritized (702). First, it is determined whether the particular medication being assessed has a history or side effect of masking cognitive impairment (704). Some medications, such as some statins, have side effects that induce cognitive impairment or mask an individual's existing cognitive impairment. If it is determined that the medication does not mask any cognitive or neurological impairment, then it will be determined whether the individual is allergic to this medication or if the likelihood of undesirable side effects (706). If it is determined that the medicine is unlikely to conflict with an individual's allergies or is unlikely to induce undesirable side effects, then it needs to be determined if there are any other potential conflicts for this particular medication (708). Conflicts may be individual person specific or a conflict might be specific to a dementia-related disease. Certain medicines might counteract any positive effects of prevention or treatment of the disease, or may conflict with therapies for other conditions or disease of that person. If it is determined that there are no conflicts for this particular medicine, then it needs to be determined whether the medication is a feasible drug (712). Feasibility consists of personal considerations, such as cost, family situation, mobility, and location. The determination of a feasible recommendation may also be specific to a person but it may also be a general determination that for whatever reason a medication is not a feasible choice. If it is determined that the medication is feasible, then for each medication (716) a dosage needs to be assessed (720). The process of assessing the dosage is described in more detail with respect to FIG. 8. If it is determined that a medication is not feasible, then it needs to be determined if there is an acceptable alternative medication (710). If there is an acceptable alternative, then that medication is assessed (702).

If it is determined that the medication does mask cognitive impairment, it needs to be determined if there is an alternative medicine with similar properties available (710). If it is determined that there is not an alternative, then the recommendation would be to refer the person to an internist (718). This situation would require special circumstances and a more specialized recommendation for the person because of particular factors, such as medical history, genetics, etc. If it is determined that there is an alternative, then the assessment process would start over (702) with the alternative medication.

If it determined that the person is either allergic to the medication or has intolerable side effects, then it would also need to be determined if there is an acceptable alternative (710). Again, if there is an alternative, then that medication would be assessed (702). If it was determined that there were conflicts with the particular medication, then it would be determined whether a decrease of the medication and/or dosage should be suggested (714). If it is determined that decrease in the medication, then the dosage of that medication would be assessed (720). If it is determined that a decrease is not necessary or possible, then it would need to be determined if there is an alternative medication (710). If there is an alternative medication, then that medication would be assessed (702).

Now referring to FIG. 8, which is a schematic flow diagram of the process (800) of assessing and updating a medication dosage recommendation. After a medication is assessed (700), then the dosage for each medication needs to also be assessed (800). The process (800) receives a medication from the process of FIG. 7, indicating that a dosage for this particular medication needs to be determined and/or adjusted. There are two overall determinations for each medicine: an existing medication process (806) and a new medication process (808). Either process may happen in any order or in parallel. It is determined whether the individual is already taking the particular medication (804). If the person is currently taking the medication, then it needs to be determined whether to increase or decrease the dosage of the medication (810). The determination to increase or decrease a medication may be determined from the process of FIG. 7, such as with conflicts, conditions of the person, etc. If it is determined to decrease the medication, the process or system describes the amount of decrease or the dosage that the medication should be decreased to, as well as the process for doing the decrease (812), which may be similar to the weaning process described below (816). It is also determined whether in the description (812), the recommended decrease is to decrease the dosage to zero (814) or take the person off the medication. If it is determined that the recommendation is to decrease the medication to zero, a weaning process is described (816). The weaning process may be individual specific or generic. The weaning process may also be included in the recommendation or priority list that is presented to the person's therapy team. After the description of the weaning process has been generated, the medication recommendation is added to the list (820). The list is the same list described as the refined recommendation and priority list of FIG. 6. Prior to the addition of the list being automatically included in the refined recommendation and priority list, it is also prioritized against other recommended medications and/or dosages.

If it is not recommended to decrease the dosage to zero, then it needs to be determined whether to adjust the base dosage for the person (822) and a recommendation for the base dosage is determined and included in the recommendation with the medication for the refined recommendation and priority list. If it is determined to increase the dosage of the medication, the recommended increase is described (818), the base dosage is adjusted (822), and the medication and dosage are added to the refined recommendation and priority list (820).

If the person is not currently taking the medication, then a process combining information about the medication (826) and variables about the person (824) are used to determine a base dosage recommendation for the person (822). The variables about the person (824) may include, but are not limited to, medical test results, conditions (e.g., other acute or chronic diseases), vitals (e.g., high/low blood pressure), genomics, demographics (e.g., age, gender, etc.), and others. After a dosage is recommended (822), the medication and dosage are added to the refined recommendation and priority list.

Now referring to FIG. 9, which is a schematic flow diagram of the process (900) describing a person's current status. Process 900 helps a doctor and a person's entire therapy team view a picture or a story of the person, their history and/or progress. First, the data descriptions, recommendations and priorities are received (902). This step may assume that the person has already previously been logged into the system, downloaded or entered pertinent information and may have already received a list of recommendations or priorities. So if a member of the person's therapy team logs into the system, information relating to that information would be loaded into the system and processed (902). The summarization processes described below may be implemented in any order or simultaneously. The descriptions pertaining to the person are summarized (904). Examples of the descriptions that are summarized include, but are not limited to, demographics, vitals, personal and family history, genomic data, biomarkers, imaging, scans, EEG results, bio-specimen test data, and/or cognitive evaluation results. Then, the behavioral history data is summarized (906). The behavioral history data may include information from personal or family interviews, or observed behaviors.

Then any previous recommendation history may be summarized (908). If the person has been logged into the system at least once, there should be at least one recommendation history to summarize. There might be multiple recommendation histories to summarize from the past. Then, the current diagnosis that has been determined by the system and/or the doctor is shown (910). The progress from the steps above is summarized and data distributions are created (912). The way that the progress, data distributions, and all of the summaries are presented may be in many different formats, targeted to the expectations and education of the person's therapy team. For example, they might be in an overall report with explanations, descriptions, graphs, time-lines, charts, etc. The information may also be presented in an interactive, computerized format. Next, any updated recommendations are created (914). The updated recommendations would come from a combination of multiple different processes discussed above, such as FIGS. 3-8. Next, based on the summaries, current diagnosis, progress, and updated recommendations, a prognosis is determined (916). The prognosis may be automatically shown to a person's therapy team or may need to be approved by a doctor or doctor's office.

One or more methods for the flow chart of FIG. 11 may be carried out on a computing device as disclosed herein. The one or more methods 1100 may include receiving user-associated data for participants, where the data relates to biological mechanisms 1110. The data may include personal and family background data, pre-existing conditions, current medications, genomic data, and diagnostic information that relate to the biological mechanisms that define dementia-related diseases as a medical condition or risk of dementia-related diseases. Some of the data may be received from electronic health records. The computing device may be a remote from the participant computing device and a device proximal the participant (either a wearable device, a device carried by the participant to which information is input, a device to which the participant inputs data, or a device to which a caregiver or provider inputs data). The computing device may be further configured to determine a freshness of the received user-associated data. For example, certain data may be historical in nature and does not change or can be updated without additional data collection from an individual person (such as date of birth), while other data may need updating on a predetermined or periodic basis. The method may include requesting updated data when the user-associated data is determined to not be fresh. The computing device may also be configured to determine whether a particular user-associated data is missing, and in response to determining a missing particular user-associated data, determine a criticality associated with the missing data. Based on the user-associated data, the computing device is configured to determine if a person is a candidate for a dementia-related disease.

The method 1100 may include receiving therapy-associated data and corresponding target biological mechanisms (1112). The therapy-associated data may include individual therapy plans that specify corresponding individual ones of the biological mechanisms that each individual therapy targets to adjust a physiological state of the corresponding biological mechanisms. The therapy-associated data contains variations found in the individual therapy's effect on the corresponding target biological mechanisms as a function of the personal background data and also contains data quantifying a probability of success of the therapy.

The method 1100 may include generating an expected adjustment of individual biological mechanisms (1118). The expected adjustment results from particular combinations of the therapies and a probability reflecting the likelihood of reaching those therapy results.

The method 1100 may include receiving diagnostic and testing data after the participant has undergone treatment according to the therapy plan to generate values associated with the biological mechanisms (1116). A comparison between the hoped-for or expected values for the biological mechanisms and the actual values for the same biological mechanisms is then made.

The method 1100 may include dynamically adjusting the therapy plan when the actual or generated values are within the hoped-for, expected, or recommend range (1118). Dynamically adjusting includes using the received diagnostic and testing data to generate the adjusted therapy plan.

One or more additional methods for the flow chart of FIG. 11 may be carried out on a computing device as disclosed herein. The methods will be described in further detail herein but are based on analysis of images and other input related to food and dietary intake of a participant. A participant's food and beverage intake is a significant "input" contributor to their day-to-day life and its changes. Other factors include sleep and exercise patterns of a participant, what the participant senses, such as what they see, hear, feel, smell, and taste, what the participant inhales, and their medication intake.

Specifics of food and beverage intake allow more specificity in understanding the participant's behavior than just asking the participant during periodic doctor visits. Food journals may be provided for insight into the food and consumption patterns, but are often painstaking and time-consuming to enter and collect to the point that data is often missed or fabricated, and use a person's observations without any characteristics such as size, color, volume, texture, and density. Images of food and beverage intake provides clear images of what was consumed and when it was consumed. For example, a participant can image food before eating, providing a time stamp of the time at about when food began being consumed, and image food after consumption, provided a "before and after" image analysis to determine what food was consumed, how much was consumed, and over what time period. This provides an ability to calculate good approximations of content, volume, calories, nutrients, and macro-nutrients: what was consumed, how much, and when. Furthermore, this provides an ability to understand compliance and adherence with the recommendations in a therapy plan.

The imaging may be performed by any suitable device. In one or more embodiments, the device may be a mobile device that has an image capturing module such as a camera for capturing the images. Additionally, the suitable device may be a wearable device that continuously images an environment of the patient, including food being consumed. The device may be configured to capture other data such as health data, or monitor movement or usage to determine when a user is exercising, sleeping, or eating.

As physiological and cognitive attributes change over time (e.g., vital signs, disease state, blood chemistry, metabolomics), understanding those changes impacts appropriately selected treatment plans. This involves understanding well the various inputs during that time—and food and beverage intake is a primary input for each person.

The one or more methods 1100 may include receiving user-associated data for participants, where the data relates to biological mechanisms 1110. The data may include personal and family background data, pre-existing conditions, current medications, genomic data, and diagnostic information that relate to the biological mechanisms that define dementia-related diseases as a medical condition or risk of dementia-related diseases. Some of the data may be received from electronic health records. The computing device may be a remote from the participant computing device and a device proximal the participant (either a wearable device, a device carried by the participant to which information is input, a device to which the participant inputs data, or a device to which a caregiver or provider inputs data). The computing device may be further configured to determine a freshness of the received user-associated data. For example, certain data may be historical in nature and does not change or can be updated without additional data collection from an individual person (such as date of birth), while other data may need updating on a predetermined or periodic basis. The method may include requesting updated data when the user-associated data is determined to not be fresh. The computing device may also be configured to determine whether a particular user-associated data is missing, and in response to determining a missing particular user-associated data, determine a criticality associated with the missing data. Based on the user-associated data, the computing device is configured to determine if a person is a candidate for a dementia-related disease.

The method 1100 may include receiving therapy-associated data and corresponding target biological mechanisms (1112). The therapy-associated data may include individual therapy plans that specify corresponding individual ones of the biological mechanisms that each individual therapy targets to adjust a physiological state of the corresponding biological mechanisms. The therapy-associated data contains variations found in the individual therapy's effect on the corresponding target biological mechanisms as a function of the personal background data and also contains data quantifying a probability of success of the therapy.

The method 1100 may include generating an expected adjustment of individual biological mechanisms (1118). The expected adjustment results from particular combinations of the therapies and a probability reflecting the likelihood of reaching those therapy results.

The method 1100 may include receiving diagnostic and testing data after the participant has undergone treatment according to the therapy plan to generate values associated with the biological mechanisms (1116). A comparison between the hoped-for or expected values for the biological mechanisms and the actual values for the same biological mechanisms is then made.

The method 1100 may include dynamically adjusting the therapy plan when the actual or generated values are within the hoped-for, expected, or recommend range (1118). Dynamically adjusting includes using the received diagnostic and testing data to generate the adjusted therapy plan. A computer system that manages therapy plans related to dementia-related diseases may be provided. The system includes at least one computing device having computer executable instructions store thereon and a remote computing device having computer executable instructions store thereon. The executable instructions are configured to receive user-associated data for participants including images of food or beverages being consumed by the participant. The instructions are configured to receive therapy-associated data for participants including individual therapy plans that specify corresponding individual ones of the biological mechanisms that each individual therapy targets to adjust a physiological state of the corresponding biological mechanisms. The therapy-associated data contains variations found in the individual therapy's effect on the corresponding target biological mechanisms as a function of the personal background data and also contains data quantifying a probability of success of the therapy. The instructions are configured to generate an expected adjustment of individual biological mechanisms resulting from particular combinations of the therapies and a probability reflecting the likelihood of reaching those therapy results. The instructions are configured to receive diagnostic and testing data associated with the participant after the participant has undergone treatment according to the therapy plan from the at least one computing device to generate values associated with biological mechanisms in the person on the received diagnostic and testing data. In response to the generated values, the instructions are configured to dynamically adjust the therapy plan to a modified therapy plan when the generated values are within a recommended range. The dynamically adjusting includes using the received diagnostic and testing data to generate the adjusted therapy plan.

In one or more embodiments, the image of the participant's food or beverage is captured by the participant. In one or more embodiments, the remote computing device is configured to determine nutritional information associated with the food or beverage from its image. In one or more embodiments, the image of the participant's food or beverage is stored in a database for comparison to images of known foods or beverages. In one or more embodiments, the image of the participant's food or beverage is analyzed by one of a person or computer to determine the food or beverage being consumed. The remote computing device may be operable to determine color, color intensity, and color variation of the food, and adjust the therapy plan based on those characteristics. The remote computing device may be operable to determine or receive information related to a mass, amount, or caloric intake of the imaged food and adjust the therapy plan based on those characteristics.

In one or more embodiments, the computer system is configured to determine frequency of meals, time of day of consumption, and other data based on the imaged food or beverage.

In one or more embodiments, the system may be provided to instruct the user whether an imaged food fits within dietary requirements for a treatment plan. Additionally, the system may be able to compare the imaged food against a food database to suggest modifications or supplements to the planned food consumption based on the imaged food and totality of information processed by the system.

One or more additional methods for the flow chart of FIG. 11 may be carried out on a computing device as disclosed herein. The one or more methods 1100 may include receiving user-associated data for participants, where the data relates to biological mechanisms 1110. The data may include personal and family background data, pre-existing conditions, current medications, genomic data, and diagnostic information that relate to the biological mechanisms that define dementia-related diseases as a medical condition or risk of dementia-related diseases. Some of the data may be received from electronic health records. The computing device may be a remote from the participant computing device and a device proximal the participant (either a wearable device, a device carried by the participant to which information is input, a device to which the participant inputs data, or a device to which a caregiver or provider inputs data). The computing device may be further configured to determine a freshness of the received user-associated data. For example, certain data may be historical in nature and does not change or can be updated without additional data collection from an individual person (such as date of birth), while other data may need updating on a predetermined or periodic basis. The method may include requesting updated data when the user-associated data is determined to not be fresh. The computing device may also be configured to determine whether a particular user-associated data is missing, and in response to determining a missing particular user-associated data, determine a criticality associated with the missing data. Based on the user-associated data, the computing device is configured to determine if a person is a candidate for a dementia-related disease.

The method 1100 may include receiving therapy-associated data and corresponding target biological mechanisms (1112). The therapy-associated data may include individual therapy plans that specify corresponding individual ones of the biological mechanisms that each individual therapy targets to adjust a physiological state of the corresponding biological mechanisms. The therapy-associated data contains variations found in the individual therapy's effect on the corresponding target biological mechanisms as a function of the personal background data and also contains data quantifying a probability of success of the therapy.

The method 1100 may include generating an expected adjustment of individual biological mechanisms (1118). The expected adjustment results from particular combinations of the therapies and a probability reflecting the likelihood of reaching those therapy results.

The method 1100 may include receiving diagnostic and testing data after the participant has undergone treatment according to the therapy plan to generate values associated with the biological mechanisms (1116). A comparison between the hoped-for or expected values for the biological mechanisms and the actual values for the same biological mechanisms is then made.

The method 1100 may include dynamically adjusting the therapy plan when the actual or generated values are within the hoped-for, expected, or recommend range (1118). Dynamically adjusting includes using the received diagnostic and testing data to generate the adjusted therapy plan.

One or more applications (software programs) or APIs may be provided for implementing one or more methods disclosed herein. The capabilities of such applications can be categorized in two ways: 1) showing information to the person under treatment (such as their current treatment plan, their current brain health and risk indices, reminders, or informational videos), and 2) providing an interface for the person under treatment to enter additional data, query their attributes, or participate in brain stimulation activities or cognitive testing. The following use cases for a mobile device or application may be provided:
  1. View therapy plan, or the current subset of it
  2. View cognitive status, such as brain health and risk indices
  3. Activities related to adherence
    a. Record medication
    b. Record lifestyle activities
    c. Log personal observations
  4. Activities related to working with a person's coaching team
    a. View and record coaching sprint and associated data
    b. Communicate with Coach—view messages, acknowledge, reply
    c. Take picture and share with coach
    d. View progress towards goal, celebrations
  5. Activities related to schedules and reminders
    a. Configure desired reminders and reminding mechanism
    b. See a reminder, repeat if not acted upon
    c. View schedule, next action
    d. View appointments
    e. Enable a vacation/abnormal schedule mode—pause reminders, notify coach
  6. Activities related to managing the device and the person's account
    a. Initial setup
    b. View, add, edit, remove caregivers, family, or study partners
    c. Authentication
    d. Payment information expired
    e. Behind on payments
    f. Terminate service An application may provide status information summarized in the form of a cognitive health index, or a cognitive or memory-loss risk index. Such indices are intended to describe in a single number an aggregate, summarizing, for example, how far a person's data values are from healthy population norms or how far physiological data values for a person are from their target optimal values. An example of a cognitive health index is the Brain Health Index (BHI) developed at the Cleveland Clinic (https://healthybrains.org/brain-check-up/). An example of a cognitive risk index is the Alzheimer's Disease Risk Index (ADRI) developed at Australian National University (http://anuadri.anu.edu.au/).

An application may provide motivational adherence, through features such as reminders of actions that need to be taken, appointments, celebrations, and the like. The application may provide motivational adherence through features that provided for support changes in lifestyle in alignment with coaching methodology, which can also show how a person's cognition is improving, or how well they are adhering to recommendations and changing lifestyle.

The application may track adherence and cognitive status. The application may do this by collecting data to support coaching, adherence, diet, lifestyle, and the like. The application may receive this data from the person themselves, provider, or coach. This data may include personal logging from any of these people on the therapy team. The application executing on the mobile device may allow for sharing of information from multiple mobile devices. In this manner, data can be gathered from multiple people under treatment. A person profile can be associated with each mobile device and allow for linking of the gathered data with the person profile. The remote computing device may then utilize the gathered data and biological mechanisms in a method similar to method 1100 or any other method disclosed herein to create or adjust a therapy plan.

The application may be configured to direct the mobile device to provide training videos or a frequently-asked-questions database that may be accessed by a participant, their provider, or coach. The application may be configured to authenticate a user by a finger print, facial recognition, or some other biometric characteristic. The application may be dynamic and personalized to current needs, coaching methodology and stage of coaching of a participant (driven from content on a server):
  If there are 12 recommendations and the participant is prepared to focus on 12, the application should show all 12.
  If they are not prepared to focus on 12 topics, the application should only show the participant what the participant should be focused on.
  This drives data collected to support coaching—this is data in addition to adherence data The application may be integrated with native environment resources, such as calendar, ehealth functions, notifications, and the like. The application is designed to be interacted with a minimum of twice a day (morning, evening), although usage at any time is permitted. The application may be configured to have a different user interface when a participant reaches a certain level of compliance.

The application may be further configured to assess the cognitive state of a participant by using a series of questions and imaging and recording the participant during a response of the participant. In this manner, the application directs a camera or other image processing module of the mobile device to capture images of the participant during a response or other data capturing event and comparing the imaged response with the provided response to detect a person' truthfulness or some other characteristic. Alternatively, the application may provide a series of games, standardized cognitive tests, or exercises that the participant responds to or interacts with to further assess the cognitive state of the participant.

The application may be provided with functionality that allows for scanning of medication packets. The medication packets may include a bar code, QR code, or SKU that links to a database for determining the medication. Alternatively, the database may be stored in the memory on the mobile device. The application may then determine compliance with the treatment plan as it relates to medication by monitoring how often medication packets are scanned, when they are scanned, what foods have been eaten before or after taking medication, and the like.

The application may be configured to send an alert if compliance is below a certain threshold or if cognitive testing shows a negative change in the person under treatment. The alert may be provided to the participant, provider, and/or friend or family member.

The application stores all sensitive information on the mobile device in encrypted form and moves all stored data to a server when able.

In another embodiment, a computer system that manages therapy plans related to dementia-related diseases is provided. The system includes at least one computing device having computer executable instructions store thereon and a remote computing device having computer executable instructions store thereon. The executable instructions are configured to receive user-associated data for persons, including at least one of personal and family background data, pre-existing conditions, current medications, genomic data, and diagnostic information that relate to biological mechanisms that define dementia-related diseases as a medical condition or risk of dementia-related diseases. The instructions are configured to receive therapy-associated data for persons including individual therapy plans that specify corresponding individual ones of the biological mechanisms that each individual therapy targets to adjust a physiological state of the corresponding biological mechanisms. The therapy-associated data contains variations found in the therapy's effect on the corresponding target biological mechanisms as a function of the personal background data and contains data quantifying a probability of success of the therapy. The instructions are configured to generate an expected adjustment of individual biological mechanisms resulting from particular combinations of the therapies and a probability reflecting the likelihood of reaching those therapy results. The instructions are configured to receive diagnostic and testing data associated with the person after they have undergone treatment according to the therapy plan from the at least one computing device to generate values associated with biological mechanisms in the person based on the received diagnostic and testing data. The instructions are configured to monitor one or more devices carried by the participant or one or more members of their therapy team, determine a level of compliance with the therapy plan based on the monitored devices, adjust the therapy plan based on the determined level of compliance and in response to the generated values, dynamically adjust the therapy plan to a modified therapy plan when the generated values are within a recommended range, where the dynamically adjusting includes using the received diagnostic and testing data to generate the adjusted therapy plan and to improve the effectiveness of future therapy plans, based on the compliance feedback.

According to one or more embodiments, the system is configured to adjust the rate that the devices are monitored based on the determined level of compliance.

According to one or more embodiments, the one or more devices is a digital assistant (such as Alexa, Cortana, Google Home, or Ski).

According to one or more embodiments, the one or more devices is a mobile device.

According to one or more embodiments, the mobile device is a smart phone, tablet, or smart watch.

According to one or more embodiments, the mobile device is a wearable device such as a fitness tracker.

According to one or more embodiments, the device is a CPAP machine.

According to one or more embodiments, the device is a glucometer.

According to one or more embodiments, a related method is also provided.

In addition, compliance monitoring does not need remote computing devices to be considered. Any feedback has value, so compliance feedback may come from interviews (such as from a coach or doctor), questionnaires or surveys (such as SF-36), and direct reports from the individuals or anyone on their therapy team.

According to one or more embodiments, the system is configured to provide an active treatment mode associated with pre-symptomatic and symptomatic people, a maintenance mode, and a preventative mode. In the active treatment mode, monitoring may occur frequently and with many measurement devices and for many biological mechanisms. In maintenance mode, the monitoring is less frequent, however, the computer system is configured to provide an alert if a trigger indicates that the person is leaving maintenance mode into a symptomatic state.

Those skilled in the art will recognize improvements and modifications to the embodiments of the present disclosure. All such improvements and modifications are considered within the scope of the concepts disclosed herein and the claims that follow.

What is claimed is:

1. A method for providing a therapy to a participant to improve cognitive health of the participant, the method comprising:
   using a monitoring server for:
      receiving participant information including two or more of personal and family background data, pre-existing conditions, current medications, genomic data, and diagnostic information, the diagnostic information relating to biological mechanisms that define dementia-related diseases as a medical condition or risk of dementia-related diseases;
      receiving therapy plan information, the therapy plan information comprising a plurality of individual therapy plans, each individual therapy plan specifying an individual biological mechanism targeted for physiological adjustment, variations found in an effect on the individual biological mechanism as a function of the participant information, and data quantifying a probability of success of the individual therapy plan;
      directing a participant device to display at least a portion of the individual therapy plan;
      receiving, from the participant device, conformance information;
      generating an aggregate therapy plan, the aggregate therapy plan targeting adjustment of a plurality of biological mechanisms using a combination of the individual therapy plans, the aggregate therapy plan comprising an aggregate probability reflecting a likelihood of achieving all targeted adjustments;

receiving diagnostic and testing data associated with the participant, the diagnostic and testing data captured after the participant has undergone treatment according to the aggregate therapy plan;

for each individual therapy plan in the aggregate therapy plan:
  determining a value corresponding to the individual biological mechanism in the participant based on the received diagnostic and testing data;
  performing a comparison of the value to a recommended range for the value, and
  based on the comparison, dynamically adjusting the individual therapy plan for the biological mechanism when the value is within the recommended range;
and
generating, for the participant, an adjusted aggregate therapy based on the individual therapy plan adjustments; and
adjusting the therapy plan information based on a success of the individual therapy plans of the participant and of other participants;
and
further administering the adjusted aggregate therapy by at least one of participant and a therapy provider.

2. The method of claim 1, wherein the participant device is operable to receive provider data from a therapy provider.

3. The method of claim 1, wherein the monitoring server is further operable to determine a freshness of the participant information.

4. The method of claim 1, wherein the monitoring server is further operable to:
  determine at least one item comprising the participant information is missing; and
  in response to determining at least one item is missing, determine a criticality associated with the at least one item.

5. The method of claim 1 further comprising using the monitoring server for receiving the participant information from electronic health records.

6. The method of claim 1, wherein another monitoring server is operable to receive participant information from the monitoring server.

7. The method of claim 6, wherein the another monitoring server is further operable to determine if the participant is a candidate for a dementia-related disease based on the participant information.

8. The method of claim 7, wherein the another monitoring server is further operable to:
  determine a level of risk for the participant; and
  determine if the participant is a viable candidate for a therapy based on a determined level of risk.

9. The method of claim 1 further comprising using the monitoring server for prioritizing the plurality of biological mechanisms based on participant information and data associated with a group of participants.

10. The method of claim 9 further comprising using the monitoring server for generating the aggregate therapy plan based on a priority of the biological mechanisms.

11. The method of claim 1 further comprising using the monitoring server for storing information regarding a participant's previous compliance with a previous aggregate therapy plan.

12. The method of claim 1 further comprising using the monitoring server for adjusting the therapy plan information based on the participant information and other participant information.

13. The method of claim 1 wherein the individual therapy plans include at least two therapy options where a second therapy option follows a first therapy option if values of the individual biological mechanism are not within the recommended range.

14. The method of claim 1 wherein the participant device is configured with a participant application software client.

15. The method of claim 14 further comprising using the monitoring server for directing the participant device to provide one or more of training videos and a frequently asked questions database that is accessible by the participant device.

16. The method of claim 14 further comprising using the monitoring server for authenticating a user by one or more of a finger print, facial recognition, and other biometric characteristic.

17. The method of claim 14, wherein the participant application software client is dynamic and personalized to current needs, coaching methodology and stage of coaching of a person.

18. The method of claim 14, wherein the participant application software client is integrated with native environment resources comprising one or more of a calendar, ehealth functions, and notifications.

19. The method of claim 1 further comprising using the monitoring server for tracking adherence to the adjusted aggregate therapy, and to show the adjusted aggregate therapy to the participant as appropriate.

20. The method of claim 1 further comprising using the monitoring server for:
  determining a participant's prognosis based on one or more of cognitive status and risk/health indices; and
  sending, to the participant device, the participant's prognosis.

21. The method of claim 1, wherein the participant device is operable for:
  receiving, at the participant device, direct data input from the participant and their therapy team; and
  receiving, at the participant device, personal logging of observations and adherence information.

22. The method of claim 1, wherein the participant device is operable for:
  prompting the participant for interaction one of a minimum of twice a day, and in morning and evening; and
  adjusting a prompting frequency based on a level of compliance.

23. The method of claim 1, wherein the participant device is operable for:
  collecting first cognitive information, the first cognitive information comprising participant answers to a corresponding one or more questions;
  collecting second cognitive information, the second cognitive information comprising one or more videos reflecting participant behavior to one or more prompts; and
  sending, to the monitoring server, the first cognitive information and second cognitive information, wherein the monitoring server is further operable for:
    receiving, from the participant device, the first cognitive information and second cognitive information; and assessing, based on the first cognitive information and second cognitive information, a cognitive state of the participant.

24. The method of claim 23, wherein the first cognitive information is further determined based on one or more of:
  participant performance in a series of games;
  participant performance in standardized cognitive tests; and
  participant performance in behavioral exercises.

25. The method of claim 1, wherein the participant device is operable for:
  scanning medication packets for one or more of a bar code, QR code, and a SKU; and
  sending, to the monitoring server, information reflecting the scanned medication packets, wherein the monitoring server is further operable for:
    receiving, from the participant device, information reflecting the scanned medication packets;
    linking to a database of medications for use in application of the therapy plan;
    designating a medication based on the database of medications and the scanned medication packets; and
    sending medication information identifying the medication to the participant device.

26. The method of claim 1, wherein the participant device is operable for:
  collecting the conformance information based on monitoring of one or more of:
    how often medication packets are scanned;
    when medication packets are scanned;
    what foods have been eaten before taking medication; and
    what foods have been eaten after taking medication; and
  sending, to the monitoring server, the conformance information, wherein the monitoring server is further operable to determine compliance information based on the conformance information.

27. The method of claim 1 further comprising using the monitoring server for:
  performing a comparison of compliance information to a threshold; and
  based on the comparison, send to the participant device, an alert, wherein the participant device is operable for:
    receiving, from the monitoring server, the alert; and
    in response to receiving the alert, prompting the participant.

* * * * *